US005638822A

United States Patent [19]

Seyed-Bolorforosh et al.

[11] Patent Number: 5,638,822

[45] Date of Patent: Jun. 17, 1997

[54] HYBRID PIEZOELECTRIC FOR ULTRASONIC PROBES

[75] Inventors: Mir Said Seyed-Bolorforosh, Palo Alto; Michael Greenstein, Los Altos, both of Calif.; Douglas Harriott, Saugus; Turuvekere R. Gururaja, North Andover, both of Mass.

[73] Assignee: Hewlett-Packard Company, Palo Alto, Calif.

[21] Appl. No.: 497,238

[22] Filed: Jun. 30, 1995

[51] Int. Cl.$^{6}$ .......... A61B 8/00

[52] U.S. Cl. .......... 128/662.03; 310/320

[58] Field of Search .......... 128/662.03, 663.01; 73/644; 310/358, 359, 322, 325, 326, 320; 367/152, 155, 156, 157

[56] References Cited

U.S. PATENT DOCUMENTS

| | | | |
|---|---|---|---|
| 4,348,904 | 9/1982 | Bautista, Jr. | 73/644 |
| 5,118,982 | 6/1992 | Inoue et al. | 310/366 |
| 5,163,436 | 11/1992 | Saitoh | 128/662 |
| 5,359,760 | 11/1994 | Busse et al. | 310/358 |
| 5,434,827 | 7/1995 | Bolorforosh | 128/662.03 |

OTHER PUBLICATIONS

Gururaja, T.R., et al., "Piezoelectric Composite Materials for Ultrasonic Transducer Applications . . . ", *IEEE Transactions on Sonics and Ultrasonics*, vol. SU-32, No. 4, Jul. 1985, pp. 499–513.

Marton, L., et al., "Methods of Experimental Physics", *Academic Press*, vol. 19, 1981, pp. 46–51.

Newnham, R.E., et al., "Connectivity & Piezoelectric–Pyroelectric Composites", *Mat. Res.* Bull. vol. 13, 1978, pp. 525–536.

Pan, W.Y., et al., "Large Piezoelectric Effect Induced by Direct Current Bias in PMN", *Japanese Journal of Applied Physics*, vol. 28, No. 4, Apr. 1989, pp. 653–661.

Redwood, M., "Transient Performances of a Piezoelectric Transducer", *The Journal of the Acoustical Society of America*, vol. 33, No. 4, Apr. 1961, pp. 527–536.

Shrout, Thomas R. et al., "Relaxor Ferroelectric Materials", *Ultrasonic Symposium*, 1990, pp. 711–720.

Smith, Wallace A., "Modeling 1–3 Composite Piezoelectric: Hydrostatic Response", *IEEE Trans. on Ultrasonics, Ferroelectrics, & Frequency Ctrl.*, vol. 40, No. 1 (Jan. 1993), pp. 41–48.

Smith, Wallace A., "The Role of Piezocomposites in Ultrasonic Transducers", *Ultrasonics Symposium*, 1989, pp. 755–766.

*Primary Examiner*—George Manuel

[57] ABSTRACT

An ultrasonic probe for coupling acoustic signals between the probe and a medium is provided. The ultrasonic probe has a piezoelectric element having a plurality of piezoelectric layers each having a different acoustic impedance. The piezoelectric layers are stacked in progressive order of acoustic impedance such that the layer with the acoustic impedance nearest to that of the medium is proximate the medium. At least one of said piezoelectric layers is made of piezoelectric composite material. The ultrasonic probe further has an electrode means for electrically coupling the piezoelectric layers to a voltage source for applying an oscillation voltage potential to each piezoelectric layer. The probe further has a control means for controlling the polarization of at least one of the piezoelectric layers.

24 Claims, 17 Drawing Sheets

5

HYBRID PIEZOELECTRIC FOR ULTRASONIC PROBES

FIELD OF THE INVENTION

The present invention relates to an ultrasonic probe for coupling acoustic signals between the probe and a medium with frequency control. More particularly, the present invention relates to an ultrasonic probe having a piezoelectric element adapted for transmitting ultrasonic energy to a medium of low acoustic impedance.

BACKGROUND

The ability to view the interior of a human body is often important for understanding and diagnosis of an illness or disease. Preferably, such viewing is done non-invasively to minimize the trauma that may be caused by an invasive method. For example, it is advantageous to view a patient's body without making incisions on the patient or breaking the patient's skin. Ultrasonic imaging equipment, including ultrasonic probes, have found widespread use for diagnosis in medicine.

Although ultrasonic imaging equipment (or system) provides a convenient and accurate way of gathering information from within a body, the accuracy and sensitivity of such ultrasonic systems are affected by the efficient transmission of acoustic energy from the system to a target in the body and the efficient reception of reflected ultrasonic energy by the receiver (such as a transducer). In ultrasonic medical imaging, typically the propagating medium (i.e., tissue) has an acoustic impedance that is different from that of the piezoelectric medium gathering or detecting acoustic signals. Such differences are often large and necessitate a means for acoustic impedance matching. The acoustic signal transmitted through the medium is only weakly reflected by the target (such as the heart in the body). For this reason, efficient acoustic coupling between the ultrasonic probe (including a transducer) and the propagating medium (tissue) is required.

Because the human body is not acoustically homogenous, depending on the target, the location thereof, and the medium, different frequencies of operation of the ultrasonic imaging system may be preferred. For example, an acoustic signal of higher frequency may provide a sharper image, but may not penetrate as deeply in the body as an acoustic signal of lower frequency. Therefore, it is desirable to provide an ultrasonic imaging system having the capability to operate under two different frequencies. U.S. Pat. No. 5,163,436 (Saitoh et al.) disclosed an ultrasonic probe system having a plurality of piezoelectric layers and a polarization control circuit means. The polarization control circuit means controls the polarity of the electric field applied to every two adjacent layers of the piezoelectric layers in the ultrasonic probe system. This is done to control the oscillation resonance frequency of the transducer or its impulse response. The system can be used to select and generate ultrasonic waves having a plurality of different frequencies. However, such a system may still have only limited usable bandwidth at each of it's resonance frequencies and have relatively long ringdown time (which is related to the length of time required for the acoustic energy to dissipate when the oscillation signal has been turned off). A long ringdown time results in unwanted signals interfering with signals of desired information, thus adversely affect the imaging resolution of the imaging system.

A high efficiency ultrasonic transducer with a wide frequency bandwidth enables the production of high quality images. Acoustic impedance-matching between the piezoelectric layer and the propagating medium facilities wideband operation and high sensitivity. The acoustic impedance mismatch between a piezoelectric layer that generates or receives acoustic energy (such as a piezoelectric ceramic, e.g., lead zirconate titanate (PZT)) and the propagating medium typically requires an impedance-matching layer for better transfer of acoustic energy from the ceramic to the medium. Some traditional ultrasonic probe systems (such as those disclosed in U.S. Pat. No. 5,163,436) have impedance-matching layers. However, the bandwidth of such traditional ultrasonic probe systems are still relatively narrow and the ringdown time is relatively long.

SUMMARY OF THE INVENTION

The present invention provides an ultrasonic probe that meets the need of improved acoustic coupling, wide bandwidth, and short ringdown time to result in high quality imaging capability. Moreover, the ultrasonic transducer of the present invention is capable of changing or controlling the oscillation resonance frequency.

The present invention provides an ultrasonic probe for coupling acoustic signals between the probe and a medium. The ultrasonic probe has a piezoelectric element having a plurality of piezoelectric layers each having a different acoustic impedance. The piezoelectric layers are stacked in progressive order of acoustic impedance such that the layer with the acoustic impedance nearest to that of the medium is proximate the medium. At least one of the piezoelectric layers is made of a piezoelectric composite material. The ultrasonic probe further has an electrode means for electrically coupling the piezoelectric layers for applying an oscillation voltage to each piezoelectric layer and has a control means for controlling the polarization of at least one of the piezoelectric layers.

The present invention further provides a method of transmitting ultrasound to a target in a medium with a transducer probe. The method includes the steps of impedance-matching a piezoelectric element of the transducer with the medium, selecting one of at least three oscillation resonance frequencies or conditions that provides the desired results in transmitting ultrasound to the target; and exciting the piezoelectric element to selectively emit the selected oscillation resonance frequency. The oscillation resonance frequency is controlled by means of controlling the polarization of at least one of said piezoelectric layers in said piezoelectric element or selectively applying an oscillation voltage to one or more of the piezoelectric layers to alter the oscillation resonance frequency of the piezoelectric element. The probe includes a piezoelectric element having at least three piezoelectric layers stacked in progressive order of acoustic impedance such that the layer with the acoustic impedance nearest to that of the medium is proximate the medium. The probe is capable of emitting at least three different oscillation resonance frequencies.

The present invention also provides a method of making an ultrasonic transducer. The method includes the steps of layering a plurality of piezoelectric layers and a plurality of electrodes together by interposing the piezoelectric layers between the electrodes to form a stack (the piezoelectric element), connecting the electrodes to a controlling means for controlling the polarization of at least one of the piezoelectric layers; and providing electrical connectors on the electrodes for connecting to an oscillation voltage for selectively activating one or more of the piezoelectric layers. Each of the piezoelectric layers has a different acoustic impedance. The piezoelectric layers are layered in progressive order of acoustic impedance such that the layer with the acoustic impedance nearest to that of the medium is proximate the medium, wherein at least one of the piezoelectric layers is made of a piezoelectric composite material.

The piezoelectric layers of the probe (or transducer) in the present invention are arranged such that they are mechanically in series. These piezoelectric layers can be connected such that they are electrically in parallel. To increase the number of oscillation resonance frequencies that can be efficiently transmitted or detected by the transducer, some of the electrical connections to the piezoelectric layers can be opened or reversed in polarity. The wide bandwidth and high efficiency is obtained because of the presence of a plurality of piezoelectric layers which gradually vary in acoustic impedance (for example, from an acoustic impedance of 33 MRayl to an acoustic impedance of 1.5 MRayl). The simplest case of a transducer according to the present invention can be made with two piezoelectric layers with a backing layer.

Typically, the acoustic impedance of the piezoelectric material suitable for making the layer with the highest impedance is a piezoelectric ceramic (e.g., lead zirconate titanate, or PZT) having an acoustic impedance of about 33 MRayl. Alternatively, the piezoelectric material can be a relaxor ferroelectric ceramic such as PMN:PT with a large electrostrictive effect and a Curie temperature close to room temperature. The layer with a lower acoustic impedance preferably has an acoustic impedance of about 7 MRayl. Such layers (particularly those with relatively low acoustic impedance) are preferably made of a piezoelectric composite material whose acoustic impedance can be tailored to have a desired acoustic impedance. Such an ultrasonic transducer will provide wide bandwidth with short ringdown time when the stress vectors are balanced between the piezoelectric layers. The poling vectors of some of the piezoelectric layers can be controlled so that they are arranged in opposite directions or in the same direction to control the transducer impulse response.

Furthermore, additional modes of operation can be obtained by turning off the oscillation voltage, and/or the quasi static polarization voltage, to some of the piezoelectric layers so that these layers behave as passive inert piezoelectric layers at the distal end of the ultrasonic transducer. When all the ceramic layers are active and arranged to respond to a high resonance frequency, the ultrasonic transducer would have higher sensitivity, narrower bandwidth, and higher frequency harmonics. Alternatively, a lower resonance frequency can be obtained by changing the direction of the poling vectors with respect to each other. When the distal layers are in the passive mode, the transducer will have a wider bandwidth, lower sensitivity, and lower high frequency harmonics. Therefore, with an ultrasonic system of the present invention, the oscillation resonance frequency of the transducer can be selected to achieve the intended imaging mode. The term "distal," when used in connection with a probe or transducer, refers to a position that is proximate the end thereof that interfaces with the medium for transmission or reception of acoustic energy.

BRIEF DESCRIPTION OF THE DRAWING

The following figures, which show the embodiments of the present invention, are included to better illustrate the ultrasonic transducer of the present invention. In these figures, wherein like numerals represent like features in the several views.

DETAILED DESCRIPTION OF THE PREFERRED EMBODIMENTS

Figure 1:
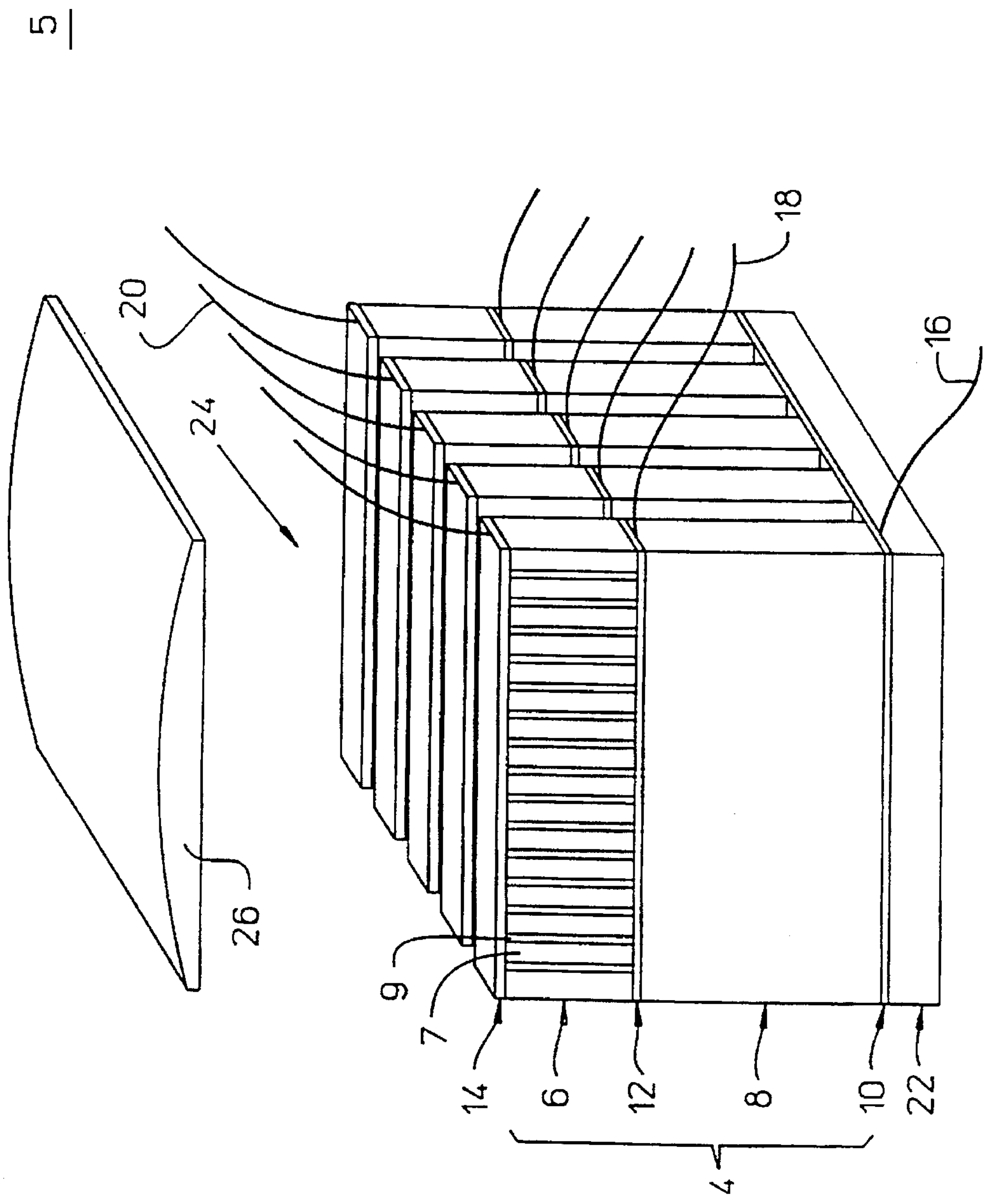
FIG. 1 is an isometric view of an embodiment of the transducer of the present invention exploded in portion.

The present invention provides a hybrid ultrasonic probe that utilizes a piezoelectric material to generate and/or detect an ultrasonic wave. The ultrasonic probe is hybrid in that it includes piezoelectric layers, one or more of which are made of a piezoelectric composite material, stacked in order of acoustic impedance. This ultrasonic probe can transmit and receive ultrasonic energy more efficiently than conventional probes to a medium of different acoustic impedance. It is also adapted to operate at a variety of oscillation frequencies (or resonating frequencies). FIG. 1 shows an isometric view of an embodiment of the ultrasonic probe according to the present invention.

Embodiment with Two Piezoelectrically Active Layers

The ultrasonic probe 1 has a piezoelectric element 4 having a plurality of piezoelectric layers (two layers 6, 8 in FIG. 1, each having a different acoustic impedance and thickness) stacked together. The piezoelectric layer 6 is made of a piezoelectric composite material. The piezoelectric layer 8 is made of solid piezoelectric material, which is PZT in this embodiment. This makes the piezoelectric ceramic structure with layers 6 and 8 a hybrid piezoelectric structure. The column-type configuration (similar to the 1–3 configuration disclosed in "Modeling 1–3 Composite Piezoelectric: Hydrostatic Response," *IEEE transactions on ultrasonics, ferroelectrics, and frequency control*, vol. 40, no. 1, January 1993, Wallace A. Smith) of piezoelectric material 7 and conformal material 9 are shown for the distal piezoelectric layer 6 for clarity. Layer 6, which is closer to the medium 5 than layer 8 during operation, has an acoustic impedance intermediate that of the acoustic impedance of the layer 8 and that of the medium. Electrodes 10, 12 are disposed on opposite sides of the piezoelectric layer 8 so that when an oscillation voltage (from oscillation voltage supply 30) is applied to layer 8, layer 8 will be excited to vibrate. Electrode 14 is disposed on the side of layer 6 opposite electrode 12 so that when an oscillation voltage is applied to layer 6 on the electrodes 12, 14, layer 6 is excited to vibrate. Wires 16, 18, 20 are connected to electrodes 10, 12 and 14, respectively, for applying electrical voltage thereto. In this configuration, the piezoelectric layers 6, 8 are connected electrically parallel to the oscillation voltage supply 30.

Preferably, the ultrasonic probe of the present invention has an array 24 of piezoelectric elements to provide a desired frequency of vibration to generate the desired acoustic signals. Each piezoelectric element in the array is connected to its respective electrodes and wires. Preferably, each of the piezoelectric elements has the same dimensions, arranged in parallel configuration, and is connected to a common electrode 10; which in turn is disposed on a backing layer 22.

To assist the transmission and reception of acoustic energy from the array 24 of piezoelectric elements to the medium 5, an acoustic lens 26 is preferably disposed on the array of piezoelectric elements at their distal ends. In this configuration, when excited, the piezoelectric elements in the array vibrate and transmit a focused beam of ultrasonic energy from the stacked piezoelectric elements through the focusing acoustic lens into the medium.

At least one, and preferably all, of the piezoelectric layers 6, 8 includes a relaxor ferroelectric ceramic that is doped to have a Curie temperature within the range of room temperature (approximately 0° C. to approximately 60° C.). Such doped relaxor ferroelectric ceramics are preferred because they provide relatively high dielectric constants. Preferably, the Curie temperature of such piezoelectric layers is near or below the room temperature (which typically is about 25° C.) such that the polarity and the magnitude of the poling vector of the layer can be controlled by applying a DC voltage thereacross. Preferably, the Curie temperature of the relaxor ferroelectric ceramic is at or below room temperature so that during application at room temperature, the plurality of the ferroelectric composite material can be reversed by the application of an appropriate voltage thereacross. Various doped or "modified" relaxor ferroelectric ceramics are known. See, for example, Shrout et al., *Proceedings of* 1990 *Ultrasonic Symposium*, pp. 711–720; Pan et al., "Large Piezoelectric In Fact Induced by Direct Current Bias in PMN: PT Relaxor Ferroelectric Ceramics," *Japanese Journal of Applied Physics*, vol. 28, no. 4, April 1989, pp. 653–661, which disclosures are incorporated by reference herein.

The piezoelectric composite materials used for making the piezoelectric layers (such as 6, 8 in FIG. 1) have a matrix of a piezoelectric ceramic (such as the relaxor piezoelectric ceramic described above) and a passive polymer such as an epoxy, polyethylene, or other suitable conformal polymers. Methods for making piezoelectric composite materials and the properties of the resulting piezoelectric composites are known, e.g., those disclosed by Wallace A. Smith, "Modeling 1–3 Composite Piezoelectric: Hydrostatic Response," *IEEE Transactions on Ultrasonics, Ferroelectrics, and Frequency Control*, vol. 40, no. 1, January 1993; Wallace A. Smith, "The Role of Piezo-composites in Ultrasonic Transduces," 1989 *IEEE Ultrasonics Symposium*, pp. 755–766 1989; and T. R. Gururaja et al., "Piezoelectric Composite Materials for Ultrasonic Transducer Applications," *IEEE Transactions on Sonics and Ultrasonics*, vol. SU-32, No. 4, pp. 499–513, July 1985, which disclosures are incorporated by reference herein.

The method of making the piezoelectric composite material, and the dimension of the piezoelectric layer made of such piezoelectric composite materials can be selected to result in a preferred frequency response caused by the stress vector conditions. Briefly, such selections can be done as follows. First, the acoustic impedance of the desired layer is chosen. Then the volume fraction of piezoelectric material (i.e., ceramic) in the composite layer together with the suitable choice of the conformal filler material is decided. This determines the dielectric constant of the composite layer. Finally, the thickness of the composite layer is selected. In the preferred mode of operation this thickness is selected so that the magnitude of the stress vector in the composite layer is equal to the magnitude of the stress vector in the solid ceramic layer. However, other thicknesses can be selected depending on the desired frequency response.

The acoustic impedance of each of the piezoelectric layers is calculated in a similar manner to the calculations of a passive acoustic impedance matching layers. One such calculation is shown in the book entitled: *Methods of Experimental Physics: Ultrasonics*, vol. 19, pp. 49–51, Ed: Peter D. Edmonds, Academic Press 1981, said method of calculation is incorporated by reference herein.

The acoustic impedance of the composite layer ($Z_{layer}$) is related to the volume fraction of the conformal material in the composite layer (V), the acoustic impedance of the conformal material ($Z_{conformal}$), and the acoustic impedance of the piezoelectric material ($Z_{PZT}$) as:

$$V=(Z_{PZT}-Z_{layer})/(Z_{PZT}-Z_{conformal}) \quad (1)$$

When a beam of acoustic energy transmitted through a body strikes a plane boundary separating two materials, some of the acoustic energy is transmitted forward and the remainder is reflected backward. The transmission coefficient is defined as:

$$\text{Transmission coefficient} = \frac{\text{Intensity of transmitted waves at the boundary}}{\text{Intensity of incident waves at the boundary}} \quad (2)$$

The reflection and transmission coefficients may be expressed either as percentages or as decreases in the number of decibels. Similarly, the reflection coefficient is an expression of the relation of the amplitude of reflected mechanical waves to that of the incident mechanical waves. It can be shown that the transmission coefficient and the reflection coefficients are related to the acoustic impedances, $Z_1$, and $Z_2$, of the two materials:

$$\text{Transmission coefficient} = \frac{2Z_2}{(Z_1+Z_2)} \quad (3)$$

$$\text{Reflection coefficient} = \frac{(Z_1-Z_2)}{(Z_1+Z_2)} \quad (4)$$

Therefore, the more similar are the acoustic impedances of the two material, the higher will be the transmission coefficient and the percentage of the acoustic energy that is transmitted through the plane boundary.

In the ultrasonic probe of the present invention, the piezoelectric element has a stack of piezoelectric layers which are stacked in progressive order of the acoustic impedance such that the most distal layer has the acoustic impedance nearest to that of the medium. In this way, the ultrasonic probe is impedance-matched with the medium to result in an efficient transmission of acoustic energy between the plane boundaries of the various layers. Preferably, the ultrasonic probe of the present invention has two or more, more preferably three or more, even more preferably three to four piezoelectric layers in the piezoelectric element so that acoustic energy can be transmitted efficiently through the ultrasonic probe. However, because of the complexity of the ultrasonic probe and the labor and skill needed to make an ultrasonic element having more than five stacked layers, the ultrasonic probe of the present invention preferably has no more than five piezoelectric layers in the piezoelectric element. However, for clarity, the embodiment of FIG. 1, which shows an ultrasonic probe of the invention having two piezoelectric layers in the piezoelectric element, is used to illustrate the ultrasonic probe of the present invention. One skilled in the art will be able to construct an ultrasonic probe with more piezoelectric layers based on the present disclosure.

Figure 2:
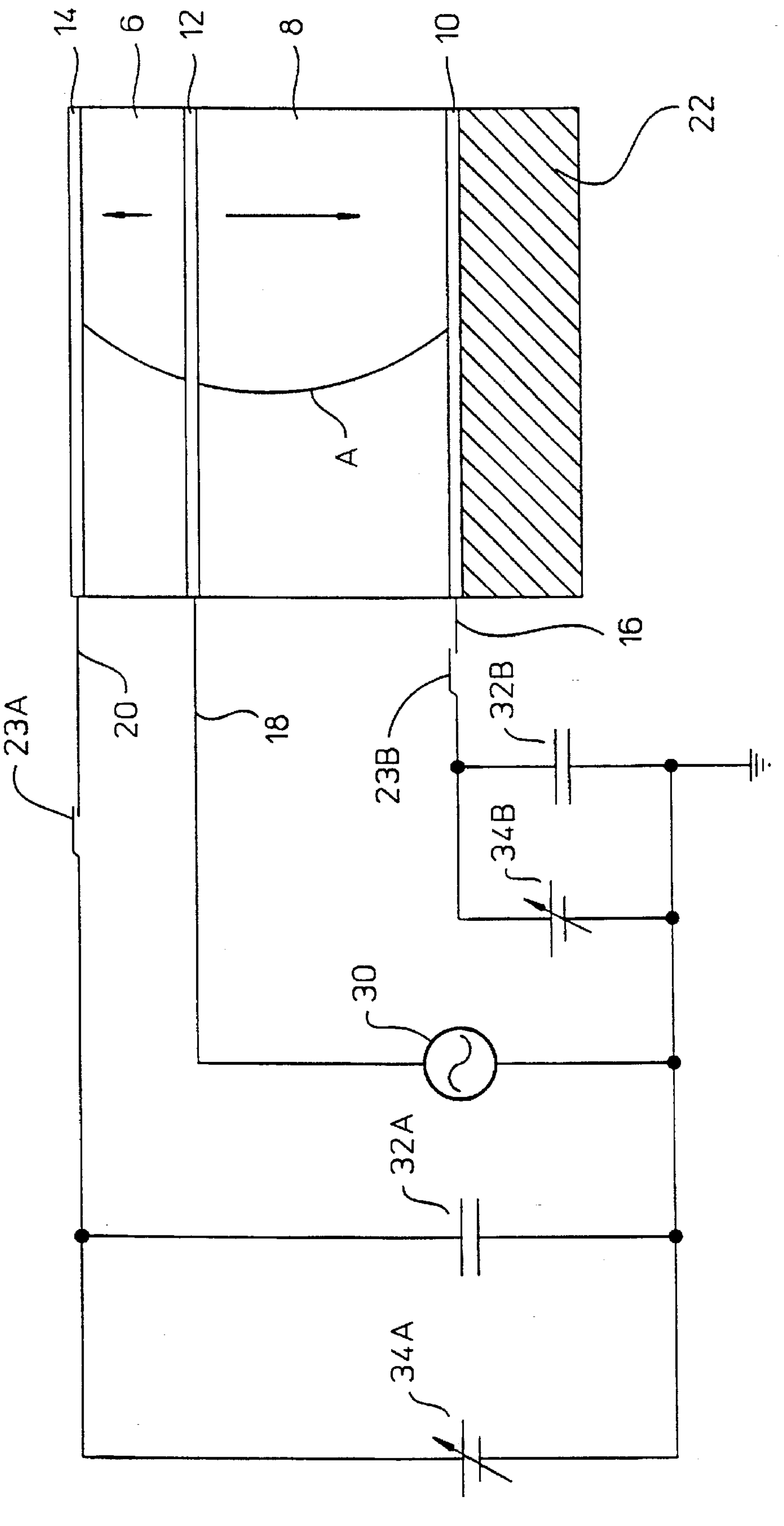
FIG. 2 is a schematic representation of an embodiment of the transducer of the present invention having two piezoelectric layers similar to FIG. 1, showing one mode of operation.

Referring to FIG. 2, the wires 18 is connected to a sinusoidal AC voltage source 30. Wire 20 is connected through a switch 23A to capacitor 32A and to an adjustable DC voltage supply 34A (in parallel). Likewise, wire 16 is connected through a switch 23B to capacitor 32B and to an adjustable DC (or variable) voltage supply 34B. The DC voltage supplies 34A, 34B, which typically have different DC polarization voltages, provides the means for controlling the polarity (or polarization) of the poling vectors of the piezoelectric layers 6, 8. The relations of DC voltage supplies 34A and 34B are such that adequate voltage difference can be applied across layer 6 and 8 to result in the desired poling vectors. Switch 23A, operatively connecting electrode 14 to the ground as related to an AC voltage, provides a means for controlling the operation of piezoelectric layer 6 (i.e., as an piezoelectrically active or passive layer). Preferably, although not necessarily, the piezoelectric layers 6 and 8 have the different thicknesses.

As shown in FIG. 2, the first mode of operation is when the two layers, under impulse excitation, would generate two stress vectors which are equal in magnitude and opposite in direction. When activated, this will generate a wave of acoustic energy. The resulting oscillation resonance frequency is $f_0$, corresponding to a half wavelength A equal to the total thickness of the layers 6 and 8.

Figure 3:
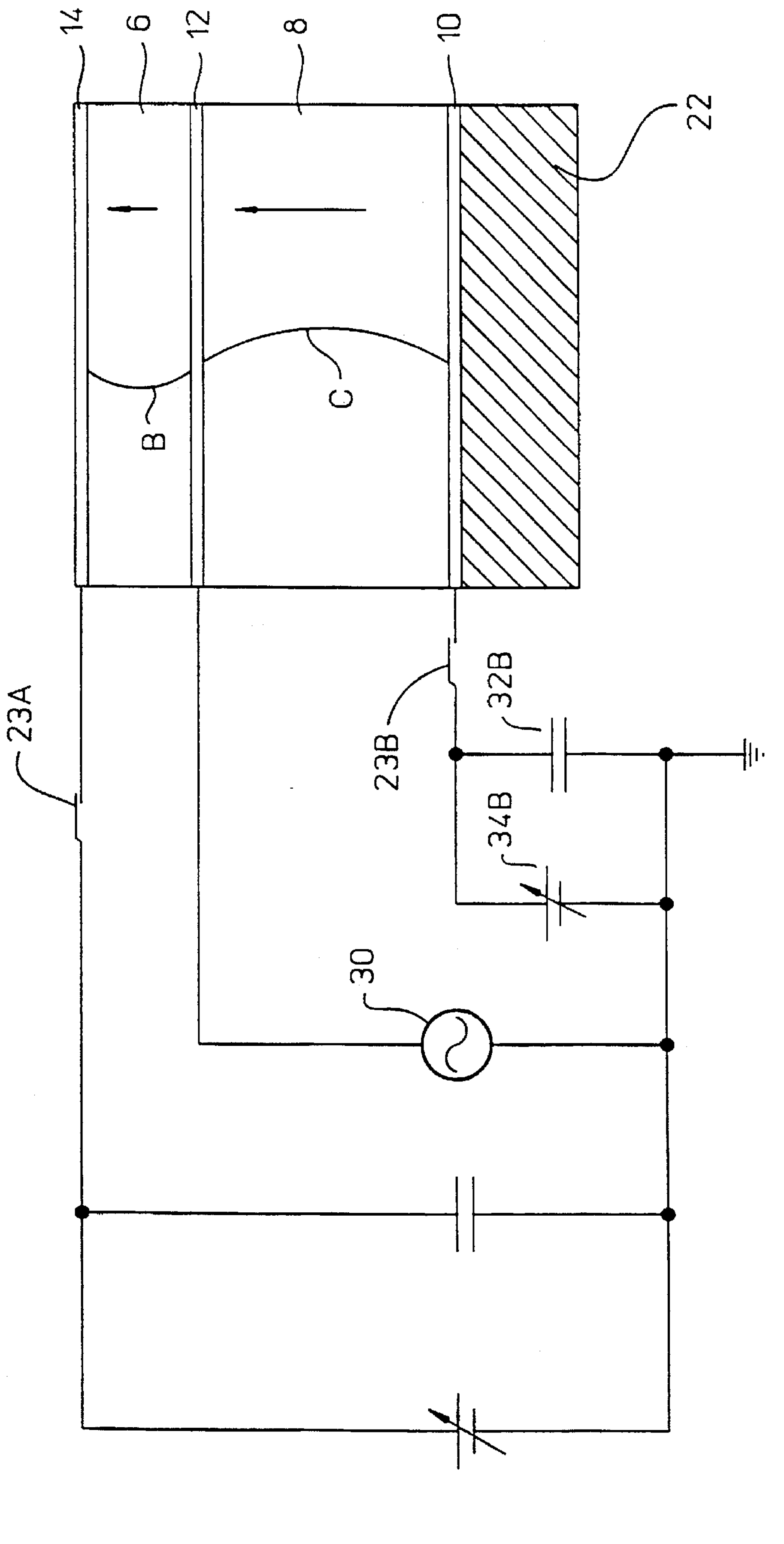
FIG. 3 is a schematic representation of the embodiment of FIG. 2 showing a second mode of operation.

Referring to FIG. 3, when the polarity of poling vector of one of the piezoelectric layers 6, 8 is reversed (by changing the DC voltage applied across that layer), stress vectors equal in magnitude and along the same direction will be generated in the two layers 6, 8. As a result, layer 6 has an oscillation resonance frequency $f_1$ corresponding to a half wavelength B equal to the thickness of layer 6. While layer 8 has an oscillation resonance frequency $f_2$ corresponding to a half wavlength C equal to the thickness of layer 8. The frequency response of this ultrasonic transducer will therefore have peaks corresponding to $f_1$ and $f_2$.

Figure 4:
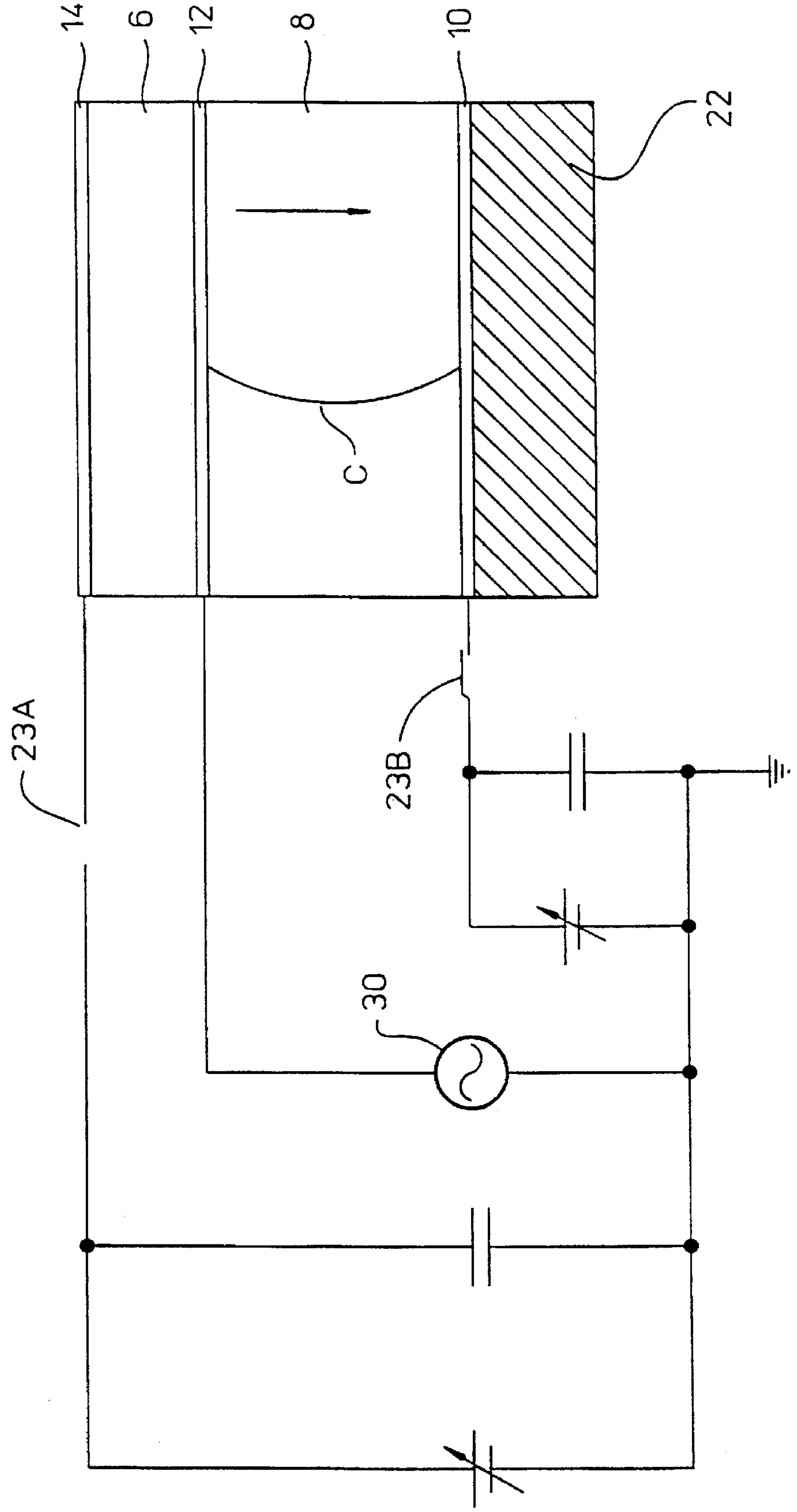
FIG. 4 is a schematic representation of the embodiment of FIG. 2 showing a third mode of operation.
Figure 5:
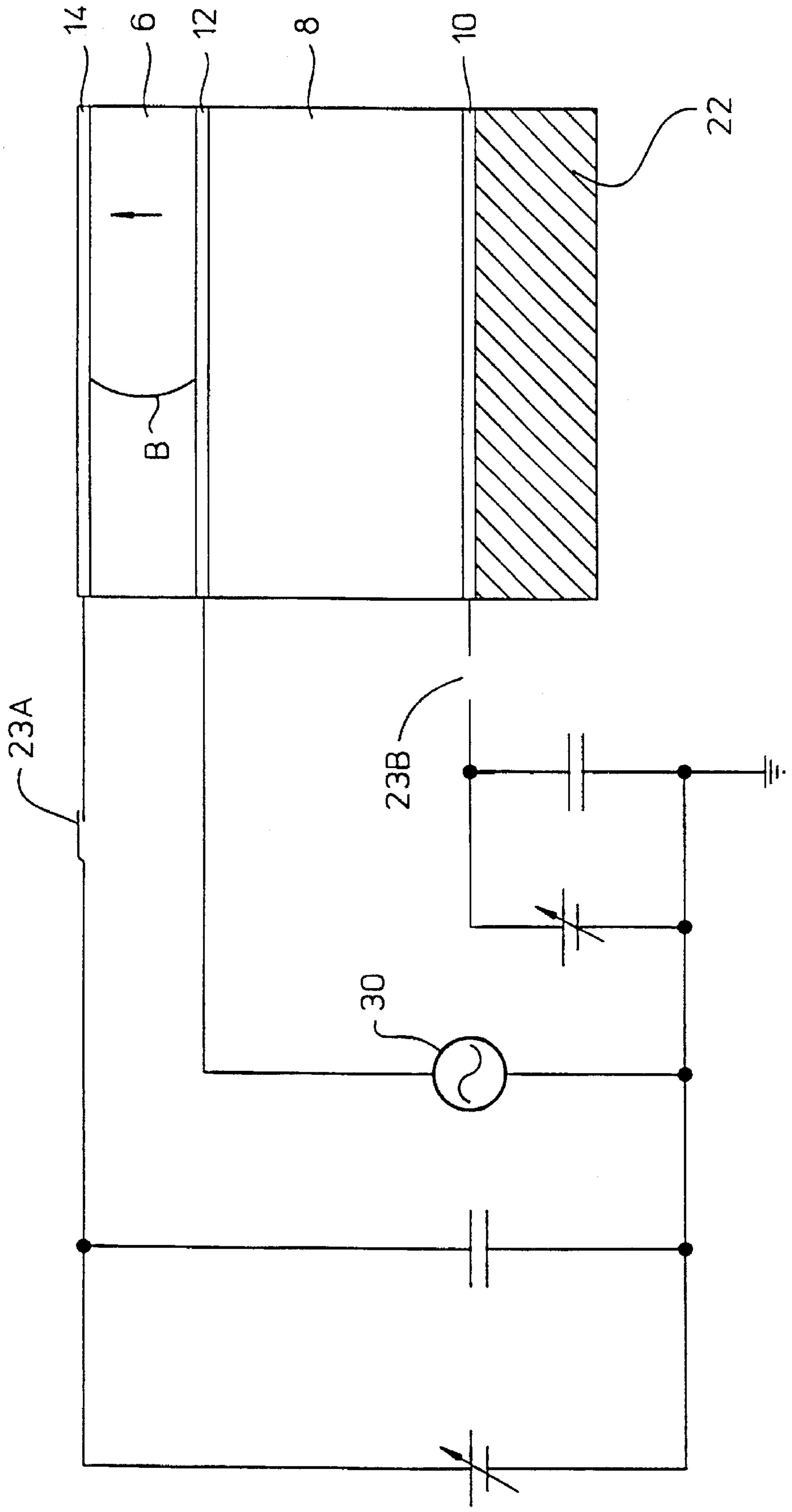
FIG. 5 is a schematic representation of the embodiment of FIG. 2 showing a fourth mode of operation.

In a third mode of operation, as shown in FIG. 4, the switch 23A can be turned off so that no electrical signal is applied to layer 6. In this way, layer 6 is piezoelectrically inactive and the resultant frequency of operation is $f_2$, corresponding to a half wavlength C equal to the thickness of layer 8. In a similar way, a fourth mode of operation is available by making layer 8 passive through turning off switch 23B (as shown in FIG. 5). This results in an oscillation resonance frequency off$_1$, corresponding to a half wavlength B equal to the thickness of layer 6.

The transducer impulse response at any of the oscillating frequencies can be further controlled by adjusting the amplitude of the stress vectors in each of the layers. In the preferred embodiment, each of the piezoelectric layers 6, 8 has about the same capacitance. However, since layer 6 preferably has a smaller thickness and dielectric constant than layer 8, the generated stress vectors are not exactly in phase and a rather complex frequency response results when both layers 6 and 8 are active. To control the transducer impulse response, preferably the magnitude and direction of the stress vectors in each layer is separately controlled. With the embodiment of FIG. 2, frequency responses of a variety of oscillating frequencies and bandwidths can be obtained. One can select the proper frequency response for the desired application.

An alternative ultrasonic probe of the present invention can be made with both layers 6 and 8 having nearly the same thickness. If the poling vectors are along the same direction, then $f_1$ and $f_2$ will be nearly equal. Moreover, when one of the piezoelectric layers 6, 8 is inactive, the oscillation resonance frequency is also $f_1$ where $f_1 \cong f_2$. This small difference is due to the difference in velocities. However, in this case, the frequency response has a wider bandwidth than when both layers 6, 8 are active. Wider bandwidth is preferred for grey-scale imaging whereas narrower bandwidth is preferred for color imaging or Doppler shift applications.

Embodiment with More than Two Piezoelectric Layers

For efficient acoustic wave transmission, preferably, the most distal layer (i.e., proximate the medium) of the piezoelectric element has an acoustic impedance that is close to that of the propagating medium. For example, if the medium is a body tissue of a patient's abdomen, which has an acoustic impudence of about 1.5 MRayl, the piezoelectric layer that is closest to the tissue has an acoustic impudence of preferably about 2–7 MRayl, depending on the number of piezoelectric layers selected to be included in the piezoelectric element stack.

Preferably, the ratio between the acoustic impedances of two adjacent piezoelectric layers in the piezoelectric element is from 1:2 to 1:6, more preferably from 1:2 to 1:4. For example, when the piezoelectric layer having the highest acoustic impedance has an acoustic impedance of 33 MRayl, the preferred acoustic impedance of the more distal impedance-matching layer in a two layered piezoelectric element is 7 MRayl (i.e, about $(33\times1.5)^{0.5}$). Preferably, the layer with the highest acoustic impedance in the piezoelectric element has an acoustic impedance of higher than 30 MRayl and the layer with the lowest acoustic impedance has an acoustic impedance of less than 2 MRayl. Such an ultrasonic probe is suitable for transmitting acoustic energy to a medium such as human tissue. In a tri-layered (i.e., not including the backing layer) piezoelectric element, the preferred acoustic impedances of the layers are respectively about 33 MRayl, 15 MRayl, and 4 MRayl. Preferably, the number of the piezoelectric layers in the piezoelectric element and their respective acoustic impedances are selected such that the acoustic impedances between two adjacent piezoelectric layers are each about 1:2 to about 1:4. The calculation and selection of acoustic impedance of each of the piezoelectric layers can be done according to *Methods of Experimental Physics: Ultrasonics,* supra.

An important factor in selecting the material for making the piezoelectric layer is the stress vectors at the boundaries between the various layers. For efficient transmission and reception of acoustic energy, it is desirable to balance the stress vectors at the interface between two adjacent piezoelectric layers in the piezoelectric element. To achieve such a balance, the layers are preferably configured such that the product of the piezoelectric constant, h (units in Volt/m or Newton/Coulomb), the clamped capacitance of the piezoelectric layer, C (units: Farad), and the voltage across the two layers, V (units: Volts), for adjacent layers are approximately equal:

$$h_1 \cdot V_1 \cdot C_1 \cong h_2 \cdot V_2 \cdot C_2$$

The piezoelectric constant, h, of a piezoelectric layer is a function of the DC voltage applied to that layer for a relaxor ferro electric ceramic. The stress vector can be controlled by controlling, for example, the thickness, the material (dielectric constant or capacitance) of construction, and the DC polarization voltage applied to the layers. After selecting the acoustic impedances for the various layers, the h and C are selected together with the proper thickness, material, and DC polarization voltage used for each piezoelectric layers. The relationship of how h is related to voltage and how C is related to the thickness is known in the art. The proper selection can be achieved with a minimal number of evaluation runs. This can be done for a transducer with two (as in the above-described embodiment) or more piezoelectric layers.

Since the same oscillation voltage, Vn, is generally applied across all the layers (i.e., n layers) and the layers are connected electrically in parallel, the product of the piezoelectric constant and the capacitance is generally tailored to ensure that the stress vectors between adjacent layers are balanced (i.e., similar). This results in a shorter ringdown time and higher sensitivity. Typically, the thicknesses and consequently the capacitances of any two adjacent piezoelectric layers in the piezoelectric element are selected so that the resulting stress vector of the two layers are within 50%, preferably within 40%, more preferably within 20% of each other, when the same oscillation voltage is applied to each of the layers. As used herein, a percentage is expressed on the basis of the larger of the two vectors. More preferably, the products of the piezoelectric constant and the capacitance for each of the layers in the piezoelectric elements are selected such that the resulting stress vectors of each (two) of the piezoelectric layers in the piezoelectric elements are substantially equal when the same oscillation voltage is applied to each of the layers.

Figure 6:
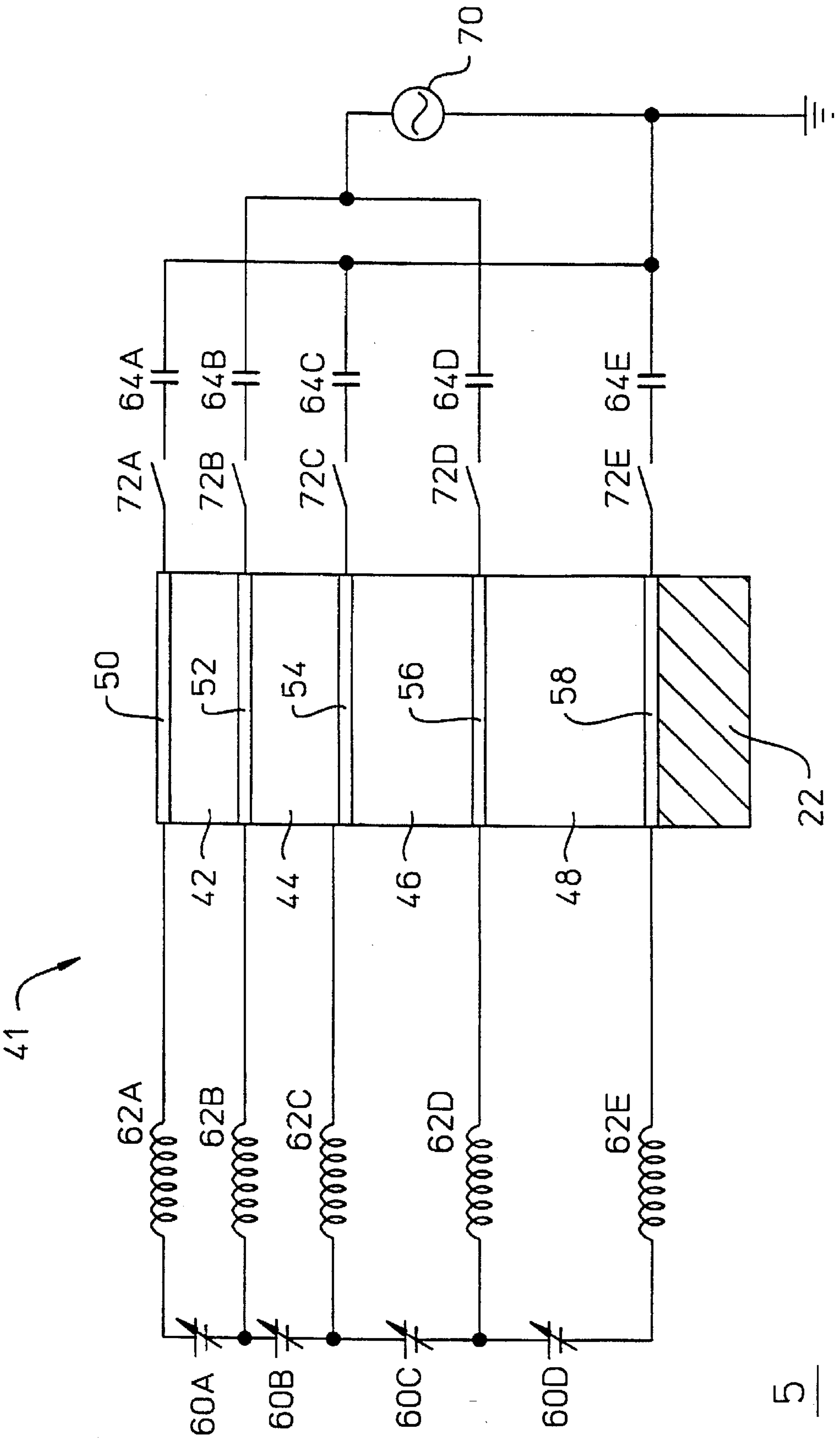
FIG. 6 is a schematic representation of another embodiment of the transducer of the present invention having four piezoelectric layers.

FIG. 6 shows a schematic representation of a preferred embodiment of the present invention. Except for the fact that it contains four piezoelectric layers and that electrical connections (including electrodes, DC supplies, capacitors, switches, and wires) corresponding to each of the layers are provided such that the proper polarity and oscillation voltage can be applied as desired, the probe of this embodiment is similar to the embodiment of FIG. 1. In FIG. 6, piezoelectric layers 42, 44, 46, 48 are stacked one on top of another with electrodes 50, 52, 54, 56, 58 connected thereto to form a stacked piezoelectric element. The electrodes 52, 54, 56, 58 are each disposed between two piezoelectric layers so that each layer can be independently turned on and off. Variable DC voltage supplies 60A, 60B, 60C, 60D are electrically connected to the electrodes 50, 52, 54, 56, 58 via a series of inductors 62A, 62B, 62C, 62D, 62E such that the polarities of the piezoelectric layers 42, 44, 46, 48 can be reversed when desired. Oscillation signal generator (i.e., AC voltage supply) 70 provides the oscillation voltage for exciting the piezoelectric layers in the piezoelectric element. Electrodes 52 and 56 are connected electrically in parallel to one pole (e.g., the signal side) of signal generator 70 while electrodes 50, 54, 58 are connected electrically in parallel to the other pole (e.g., the ground). The capacitors 64A, 64B, 64C, 64D, 64E permits the AC signal to pass while isolating the DC voltages. Switches 72A, 72B, 72C, 72D, 72E connected to the electrodes enable selective application of the oscillation voltage to one or more of the piezoelectric layers to cause vibration.

Figure 7:
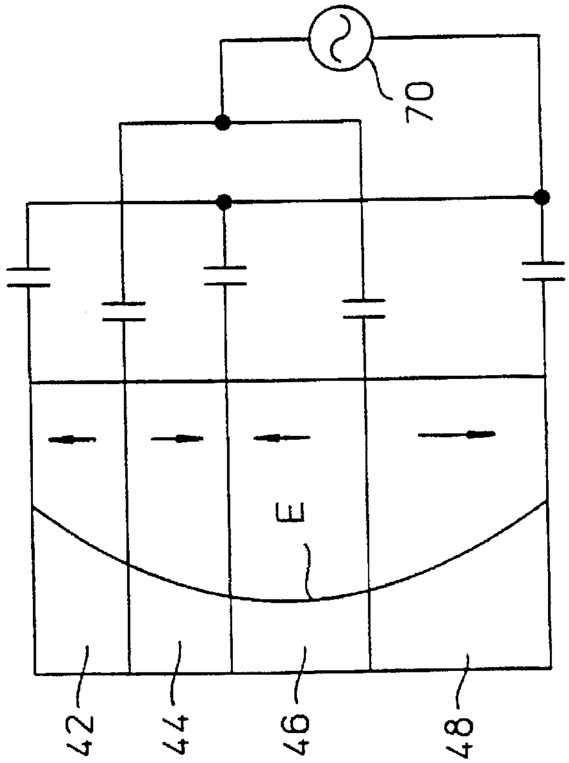
FIG. 7 is a schematic representation of the embodiment of FIG. 6 showing one mode of operation.

By controlling the switches 72A, 72B, 72C, 72D, 72E, as well as the variable DC voltage supplies 60A, 60B, 60C, 60D, the piezoelectric element can be made to transmit or receive acoustic waves at different frequencies. Referring to FIG. 7, which shows a schematic representation of the ultrasonic probe of FIG. 6, the DC voltage supplies are controlled so that the poling vectors of any two adjacent piezoelectric layers are in the opposite direction. In this configuration, the piezoelectric element is most adapted to respond to an oscillation resonance frequency having a half wavelength E that is equal to the thickness of the stack encompassing layers 42, 44, 46, 48.

Figure 8:
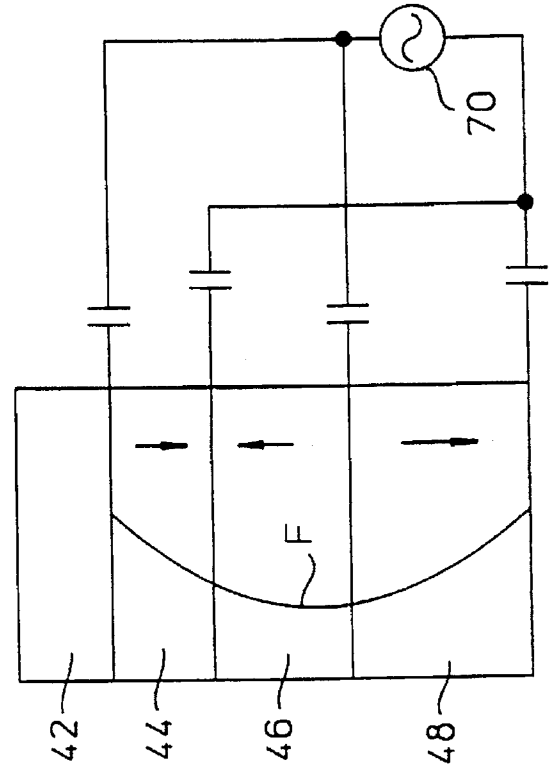
FIG. 8 is a schematic representation of the embodiment of FIG. 6 showing a second mode of operation.
Figure 10:
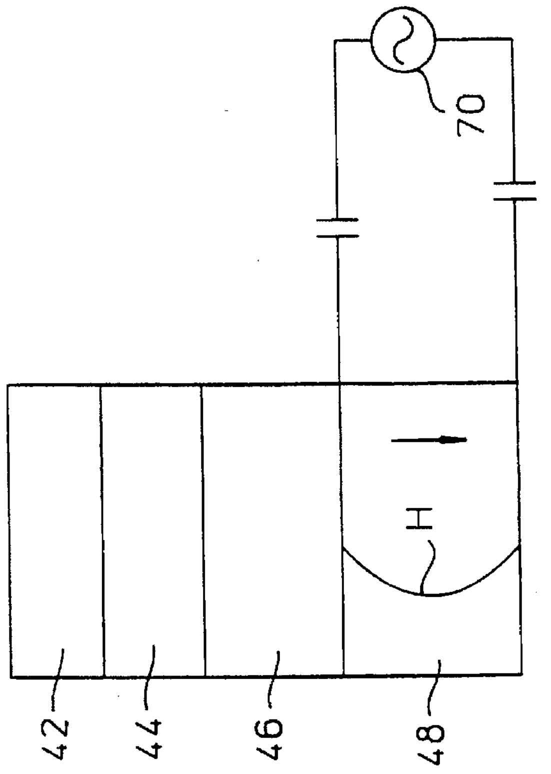
FIG. 10 is a schematic representation of the embodiment of FIG. 6 showing a fourth mode of operation.
Figure 9:
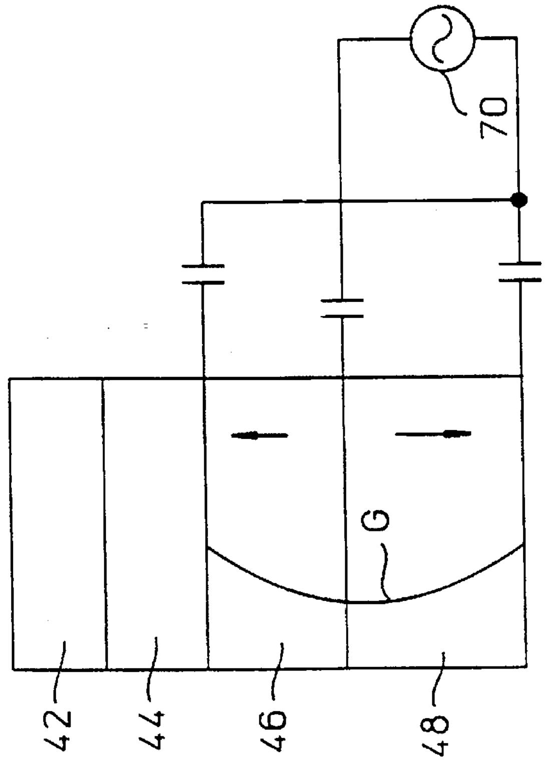
FIG. 9 is a schematic representation of the embodiment of FIG. 6 showing a third mode of operation.

Referring now to FIG. 8, the switch 72A of FIG. 6 is selectively opened to turn off the piezoelectric layer 42, and the poling vectors of the piezoelectrically active layers remain the same as in FIG. 7. This piezoelectric element is most adapted to respond to an oscillation resonance frequency corresponding to a half wavelength F equal to the thickness of the sum of the most proximal 3 layers 44, 46, 48. Similarly, referring to FIG. 9, when the distal two layers 42, 44 are turned off by opening the switches 72A, 72B and the oscillation voltage is applied to the most proximal two piezoelectric layers 46, 48 which have oppositely directing poling vectors, the piezoelectric element is most adapted to respond to an oscillation resonance frequency corresponding to a half wavelength G equal to the thickness of the most proximal two layers 46, 48. In the same way, as shown in FIG. 10, when the ultrasonic probe system on FIG. 5 is controlled so that when the oscillation voltage is applied to the most proximal piezoelectric layer 48, the piezoelectric element is most adapted to respond to an oscillation resonance frequency corresponding to a half wavelength H equal to the thickness of that most proximal layer.

In addition to opening the switches to render some of the piezoelectric layers passive as in FIGS. 7, 8, 9, and 10, the ultrasonic probe system on FIG. 6 can be made to respond to different oscillation resonance frequencies by selectively changing the direction of the poling vectors of some of the piezoelectric layers in the piezoelectric element. This is accomplished by controlling the DC voltage supplies 60A, 60B, 60C, 60D. In this manner, the same oscillation voltage is applied across each of the piezoelectric layers 42, 44, 46, and 48.

Figure 11:
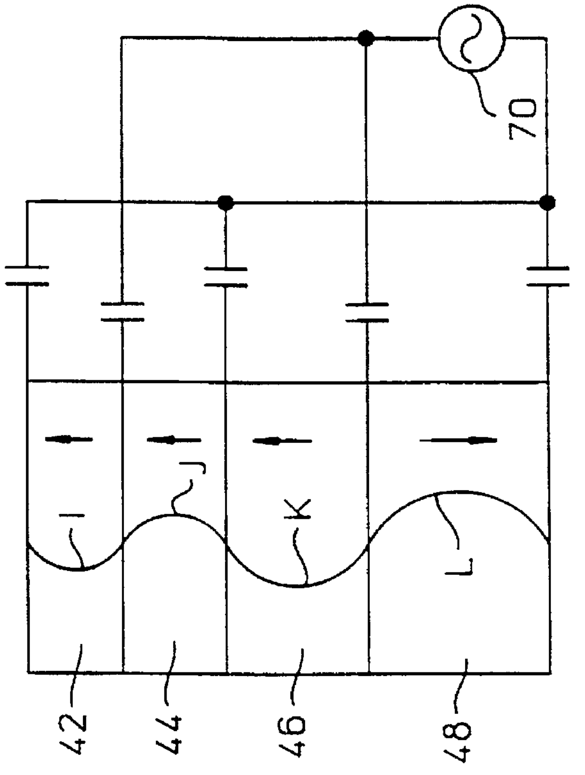
FIG. 11 is a schematic representation of the embodiment of FIG. 6 showing a fifth mode of operation.

By controlling the poling voltages (the DC supplier 60A, 60B, 60C, 60D), the poling vectors of the piezoelectric layers can be controlled so that one or more of the layers have poling vectors that are in the same direction or opposite direction. Referring to FIGS. 6 and 11, the piezoelectric layers are all connected in parallel to the signal generator 70. However, the poling vectors are controlled independently. In FIG. 11, all the piezoelectric layers have poling vectors in the same direction. Thus, each of the piezoelectric layers 42, 44, 46, 48 will have a different frequency ($f_{11}$, $f_{12}$, $f_{13}$, $f_{14}$ corresponding to half wavelengths I, J, K, L for layers 42, 44, 46, 48 respectively).

Figure 12:
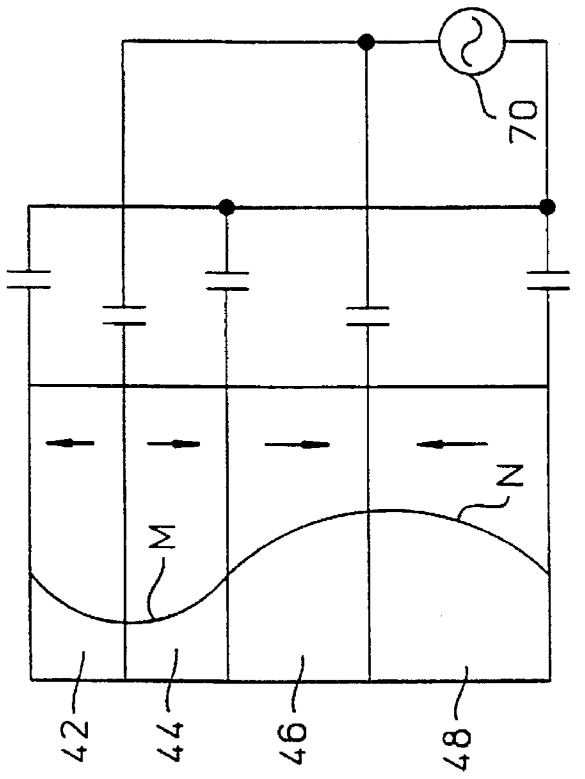
FIG. 12 is a schematic representation of the embodiment of FIG. 6 showing a sixth mode of operation.
Figure 13:
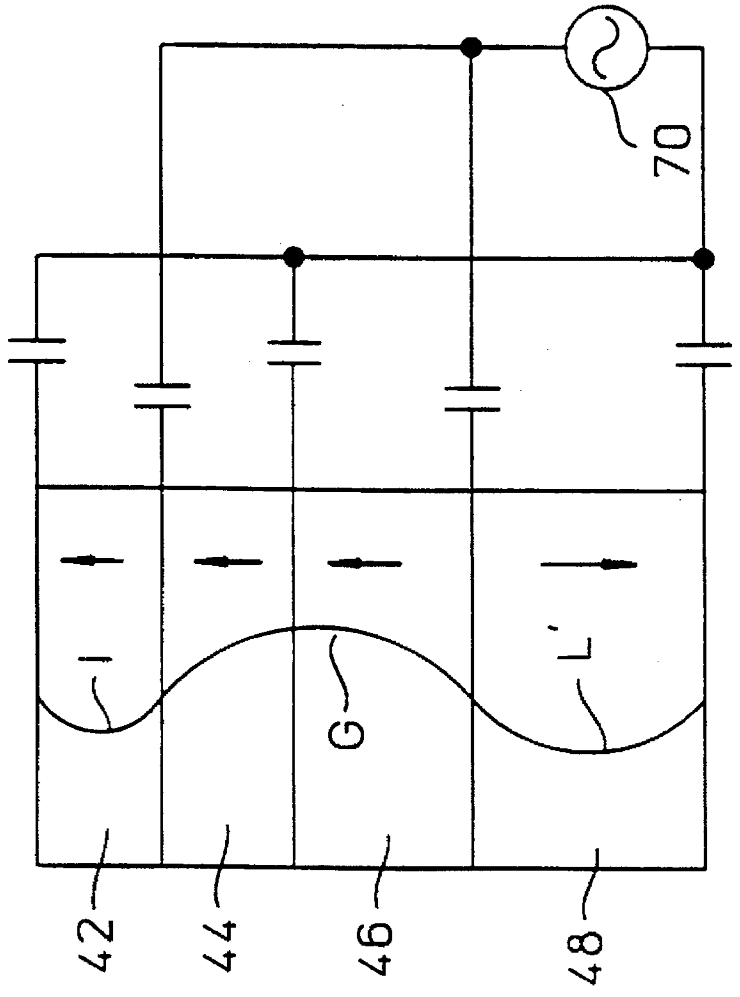
FIG. 13 is a schematic representation of the embodiment of FIG. 6 showing a seventh mode of operation.

Referring to FIG. 12, wherein the oscillation voltage is applied to the piezoelectric layers in a similar way as that of FIG. 6 and 11, the variable DC supplies are controlled so that the most distal two piezoelectric layers 42, 44 have poling vectors in the opposite directions and the most proximal two layers 46, 48 have poling vectors in opposite directions. The intermediate two layers 44, 46 have poling vectors that are in the same direction. Thus, the distal two piezoelectric layers 42, 44 will together have an oscillation resonance frequency $f_{15}$, and the proximal piezoelectric layers 46, 48 will together have an oscillation resonance frequency $f_{16}$, corresponding to half wavelengths M and N respectively. In FIG. 13, the piezoelectric layers are controlled in a manner similar to the above embodiments such that the distal two layers 42, 44 have poling vectors in the same direction, which is opposite to the direction of the proximal two layers 46, 48. As a result, the most distal layer 42, the intermediate layers 46, 48, and the proximal layer 48 have 25 oscillation resonance frequencies $f_{11}$, $f_{17}$, and $f_{14}$ corresponding to half wavelengths I, Q, and L' respectively.

Comparing the frequency response of the configurations shown in FIG. 11, 12, and 13, the larger the number of different oscillating frequencies (for example, FIG. 11) the wider would be the frequency bandwidth. However; the more layers excited to operate at the same frequency (for example, FIG. 7) would result in higher. Hence, it is a compromise between the sensitivity and bandwidth.

The following example is provided to illustrate the operation of an ultrasonic probe system of the present invention.

EXAMPLE

Figure 14:
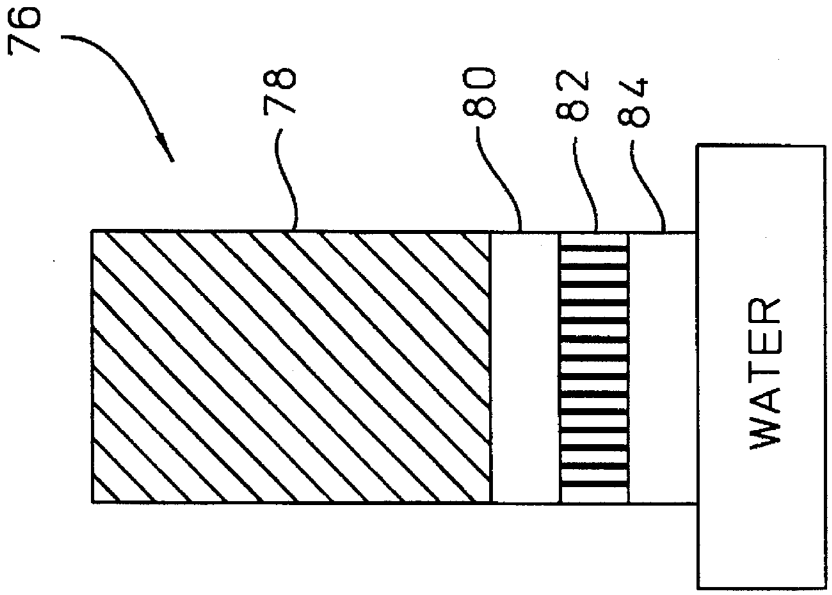
FIG. 14 is a schematic representation of an embodiment of the present invention as applied to water in operation.
Figure 15:
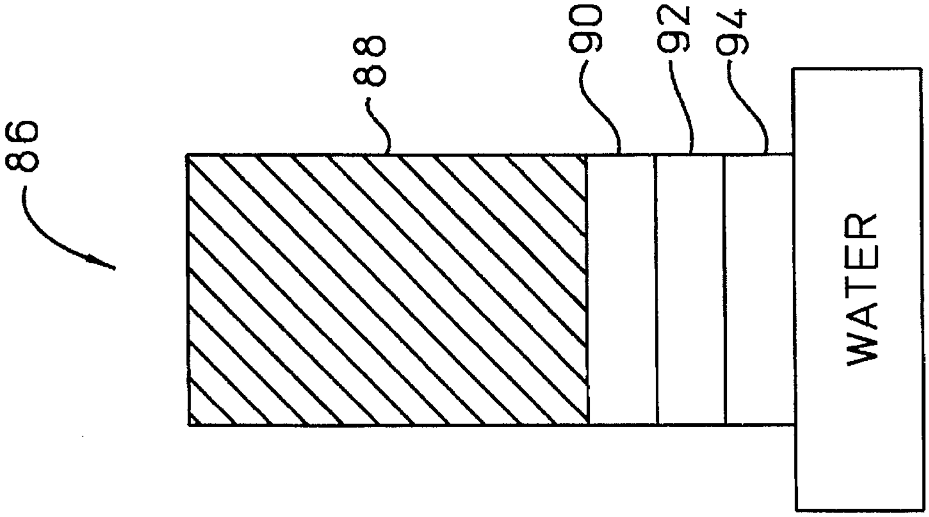
FIG. 15 is a schematic representation of an embodiment of a conventional transducer as applied to water in operation.

To illustrate the advantages of the present invention and compare it with the conventional device with clarity, a computer simulation of a ultrasonic transducer having two piezoelectric layers is performed. The transducer structures (conventional vs. hybrid) for the two simulations are shown in FIGS. 14 and 15. Water is the transmission medium in the simulations. The parameters for the two transducers are tabulated in Table 1 below. The impulse response was simulated using a digital computer simulating the transducer impulse response based on the model proposed by Redwood as described in; "Transient performance of a piezoelectric transducer", by M. Redwood, the *Journal of Acoustical Society of America*, Vol. 33, No. 4, pp. 527–536, 1961, whose disclosure relating to the model is incorporated by reference herein. This model describes the transient impulse response for an ultrasonic transducer.

TABLE 1

Transducer simulation design characteristics

| | Conventional transducer | Hybrid (new) transducer |
|---|---|---|
| Acoustic Impedance of the backing layer (MRayl) | 8 | 8 |
| Acoustic Impedance of first piezoelectric layer (MRayl) | 33 | 33 |
| Acoustic Impedance of second piezoelectric layer (MRayl) | 33 | 12 |
| Acoustic impedance of quarter wavelength impedance matching layer (MRayl) | 7 | 3 |
| Acoustic impedance of front loading (MRayl), water | 1.5 | 1.5 |
| Thickness of ceramic layer one (micro meter) | 200 | 296 |
| Thickness of ceramic layer two (micro meter) | 200 | 154 |
| Thickness of front impedance matching layer (micro meter) | 128 | 158 |
| Attenuation of front impedance matching layer (dB/cm.MHz) | 2.8 | 2.8 |
| Electrical impedance of source (Ohm) | 50 | 50 |
| Electrical impedance of receiver (Ohm) | 50 | 50 |
| Element width (mm) | 0.15 | 0.15 |
| Element height (mm) | 10 | 10 |
| Piezoelectric material type for layer one | 100% solid ceramic | 100% solid ceramic |
| Piezoelectric material type for layer two | 100% solid ceramic | piezo-composite, 35% ceramic, 65% polymer |
| Relative dielectric constat of ceramic layer one | 3800 | 3800 |
| Relative dielectric constat of ceramic layer two | 3800 | 1330 |
| Electromechanical coupling coefficient, $K_t$, for layer one | 0.69 | 0.69 |
| Electromechanical coupling coefficient, $K_t$, for layer two | 0.69 | 0.73 |
| The piezoelectric constant, h, for layer one (Newton/coulomb) | 1.367*10⁹ → $1.367*10^9$ | $1.367*10^9$ |
| The piezoelectric constant, h, for layer two (Newton/coulomb) | $1.367*10^9$ | $1.51*10^9$ |
| Capacitance for ceramic layer one (F) | $2.522 \times 10^{-10}$ | $1.7 \times 10^{-10}$ |
| Capacitance for ceramic layer two (F) | $2.522 \times 10^{-10}$ | $1.204 \times 10^{-10}$ |

The two way impulse response for these two transducers was simulated. The result of this simulation shows the advantage of the proposed transducer design over conventional transducer designs such the given transducer design is typically optimized using simulation programs.

FIG. 14 is a schematic representation of a hybrid transducer 76 as applied to water. The transducer has a backing layer 78, a PZT ceramic layer 80, a PMN:PT composite ceramic layer 82 and a quater wavelength impedance matching layer 84. PMN represents a substance expressed by the following chemical formula: $Pb(Mg_{1/3}Nb_{2/3})O_3$ and PT represents a substance (lead titanate) expressed by the following chemical formula: $PbTiO_3$. FIG. 15 is a schematic representation of a conventional transducer 86 as applied to water. This transducer 86 has a first PZT ceramic layer 90, a second PZT ceramic layer 92, and a quater wavelength impedance matching layer 94.

Figure 16:
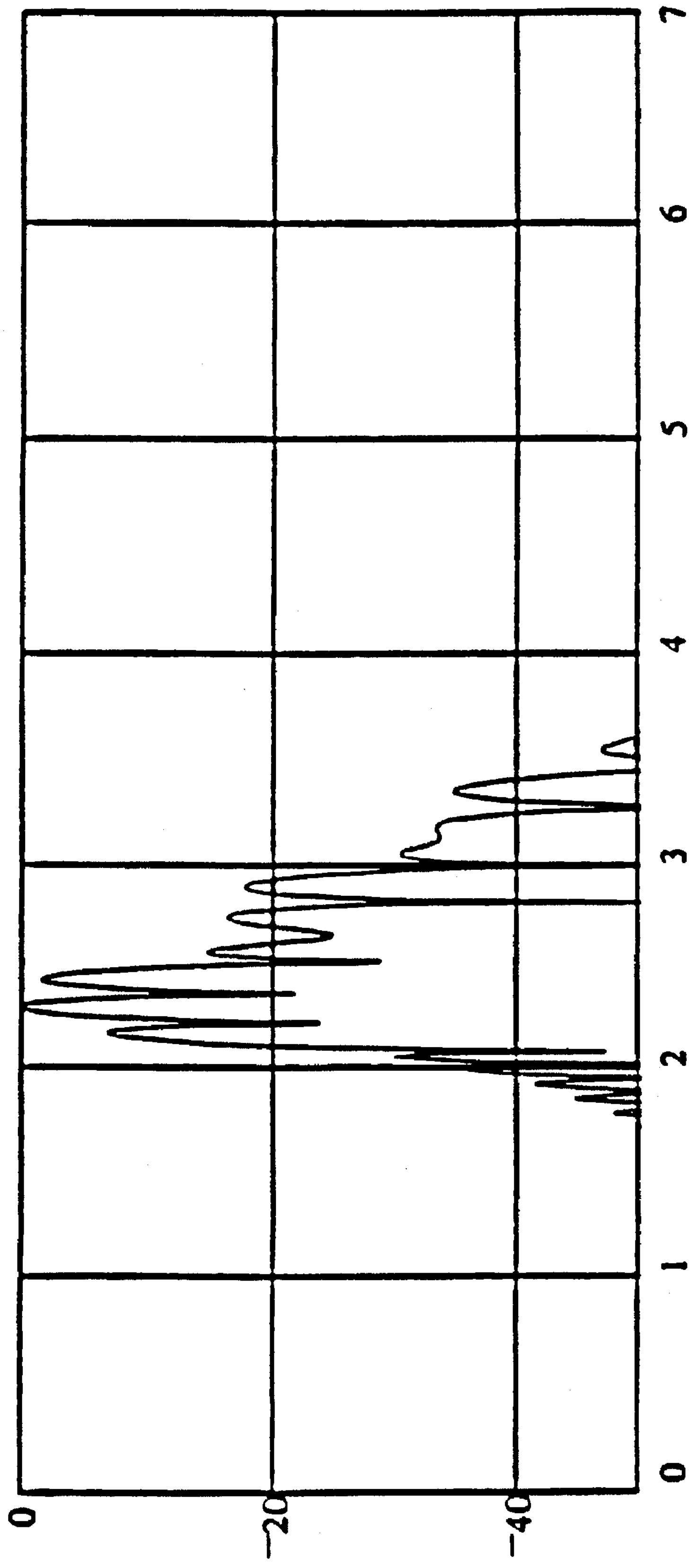
FIG. 16 is a graphical representation of the time domain impulse response of the embodiment of the transducer of the present invention of FIG. 14 with the amplitude shown in dB.
Figure 17:
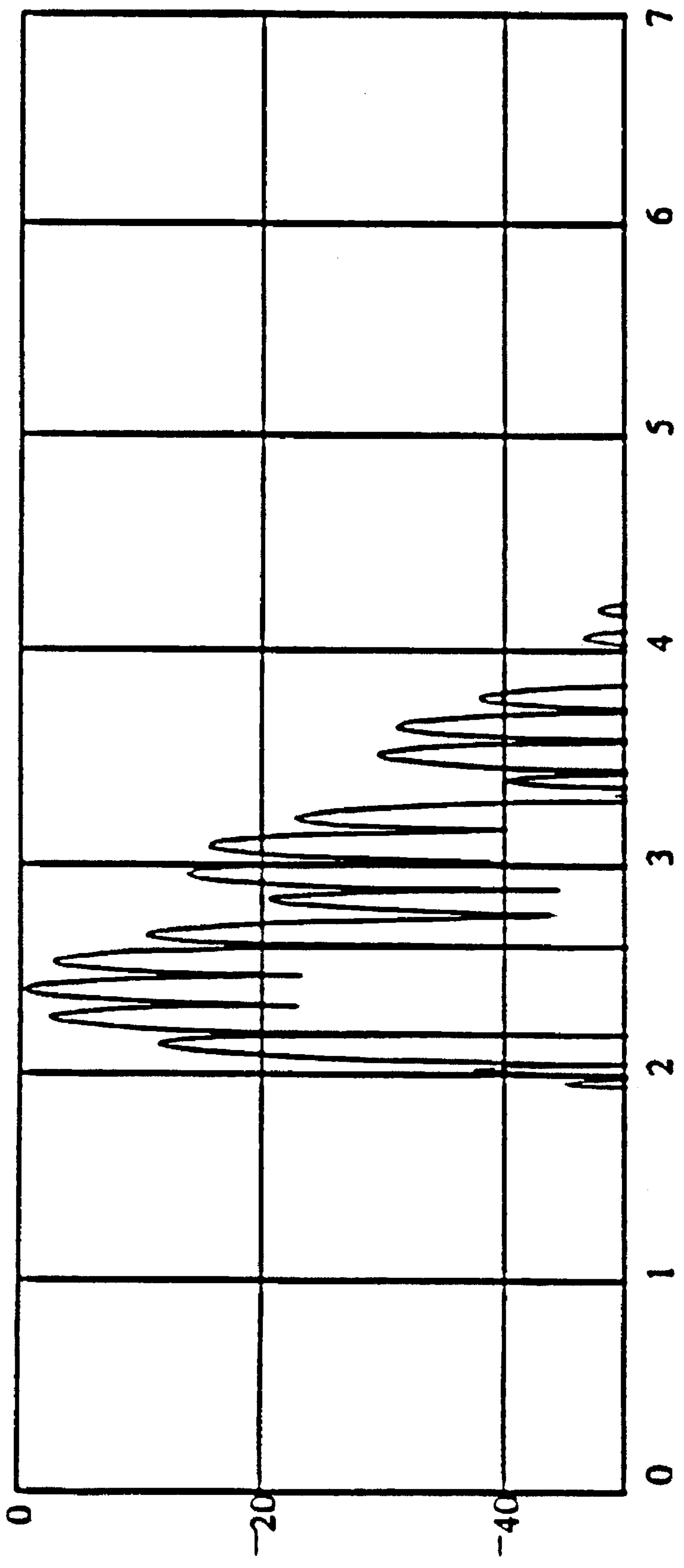
FIG. 17 is a graphical representation of the time domain impulse response of the embodiment of the conventional transducer of FIG. 15 with the amplitude shown in dB.
Figure 18:
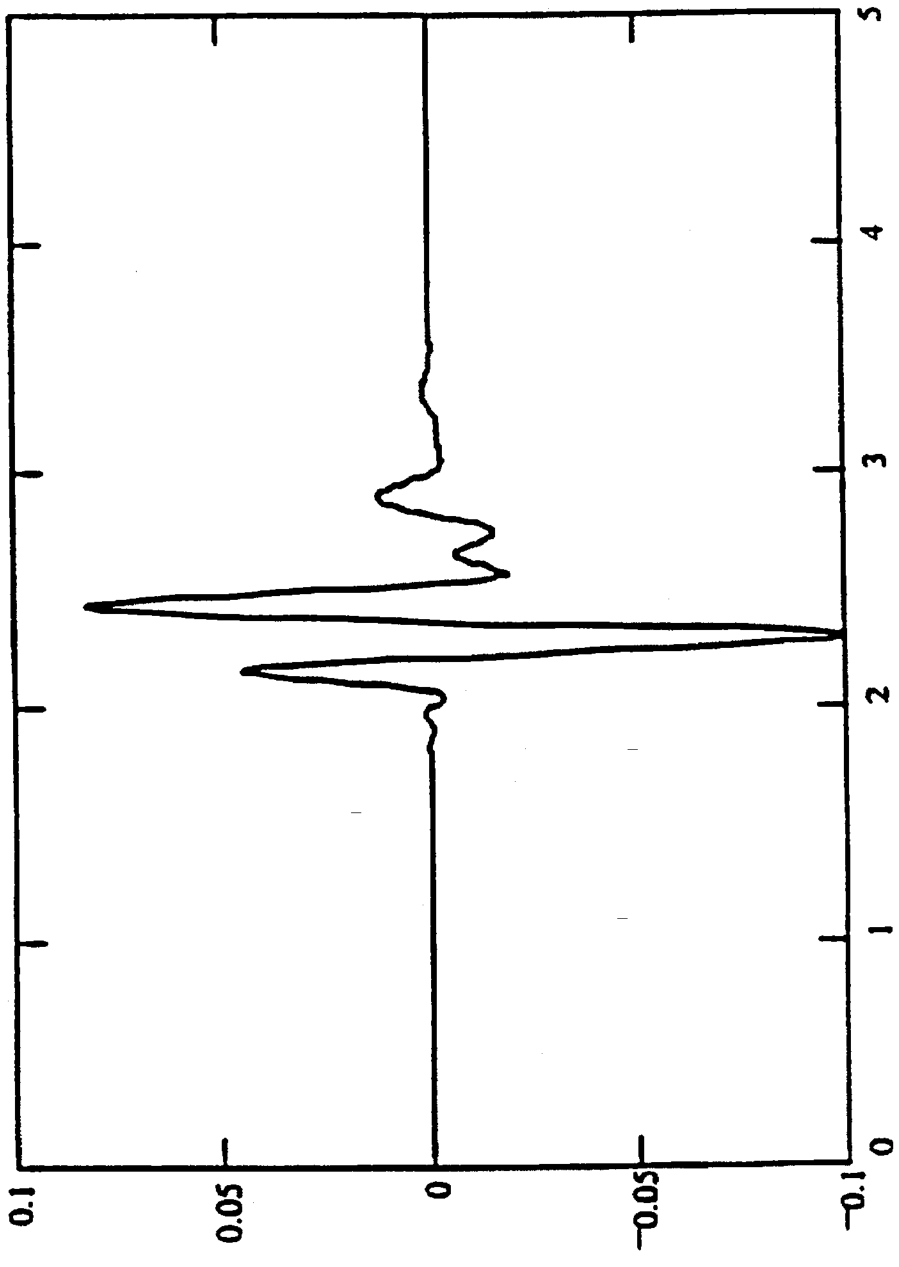
FIG. 18 is a graphical representation of the time domain impulse response of the embodiment of the transducer of the present invention of FIG. 14 with the amplitude shown in units of Volts.
Figure 19:
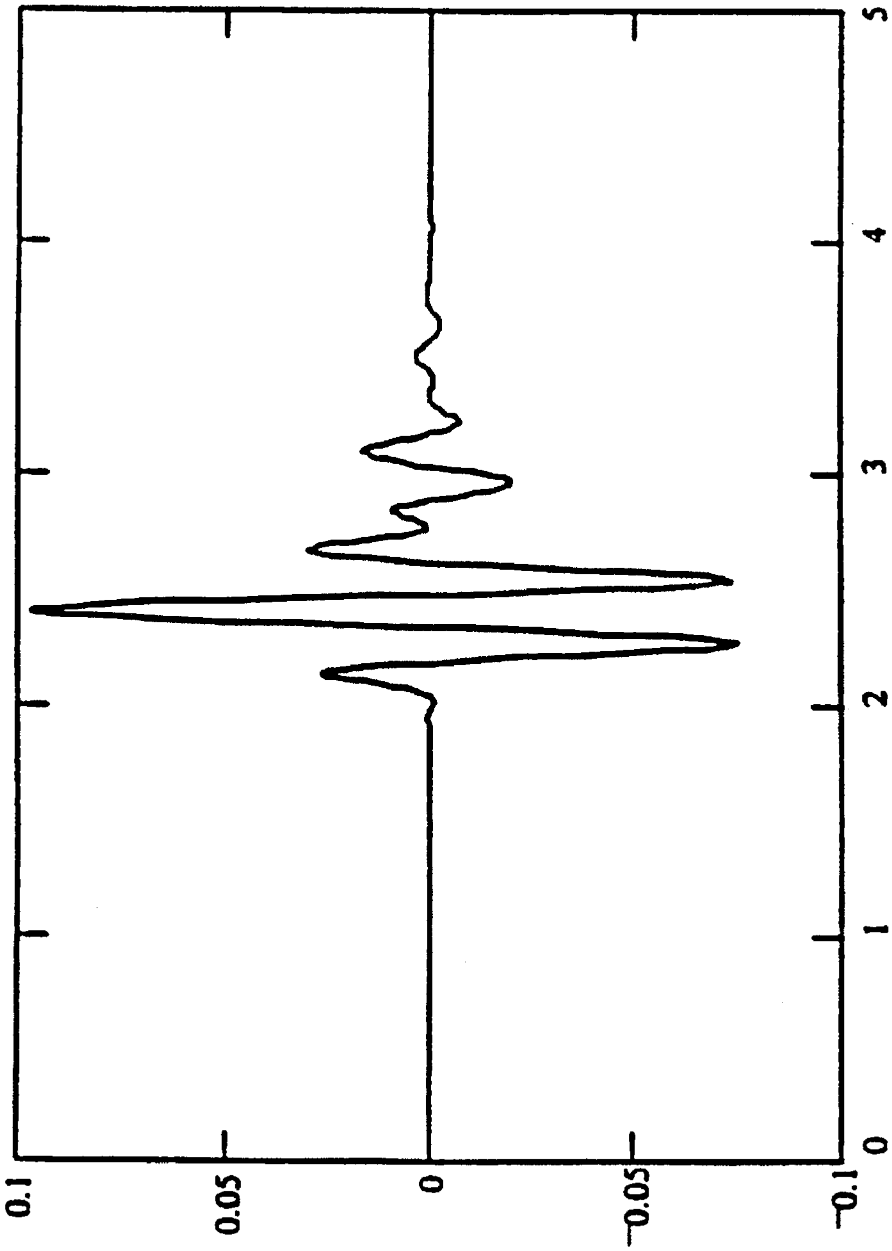
FIG. 19 is a graphical representation of the time domain impulse response of the embodiment of the conventional transducer of FIG. 15 with the amplitude shown in units of Volts.
Figure 20:
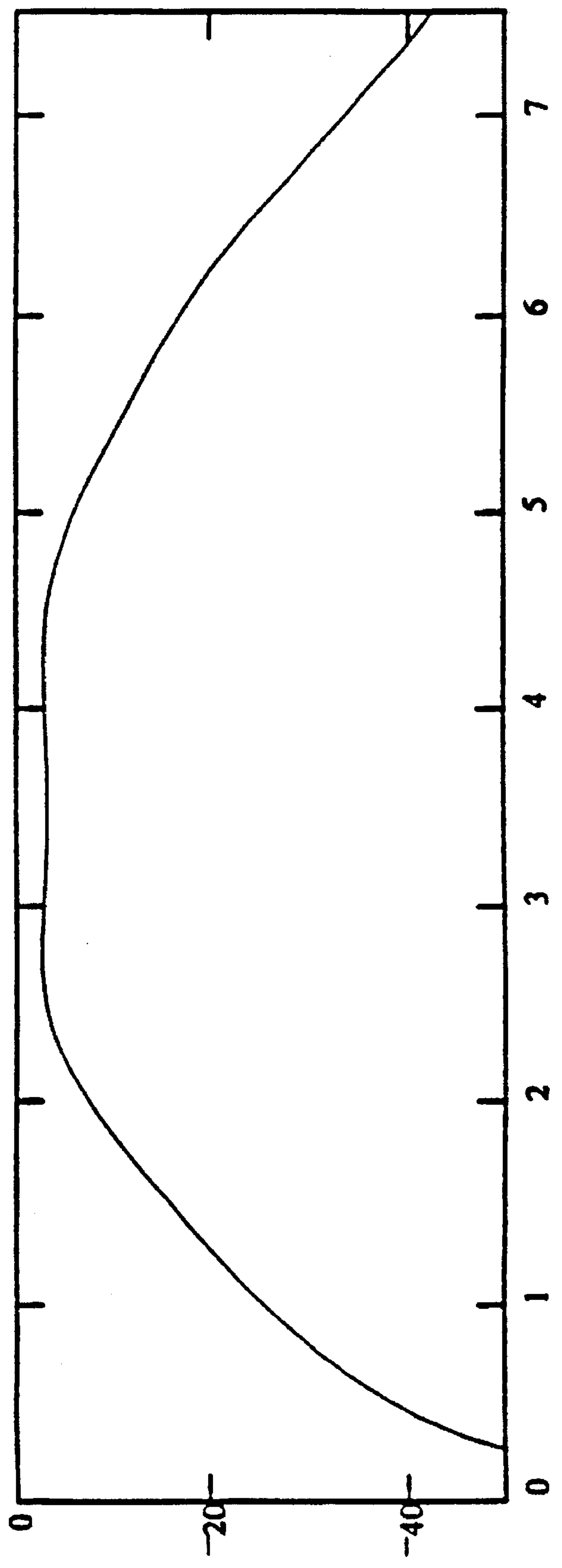
FIG. 20 is a graphical representation of the frequency domain impulse response of the embodiment of the transducer of the present invention of FIG. 14 with the amplitude shown in dB.
Figure 21:
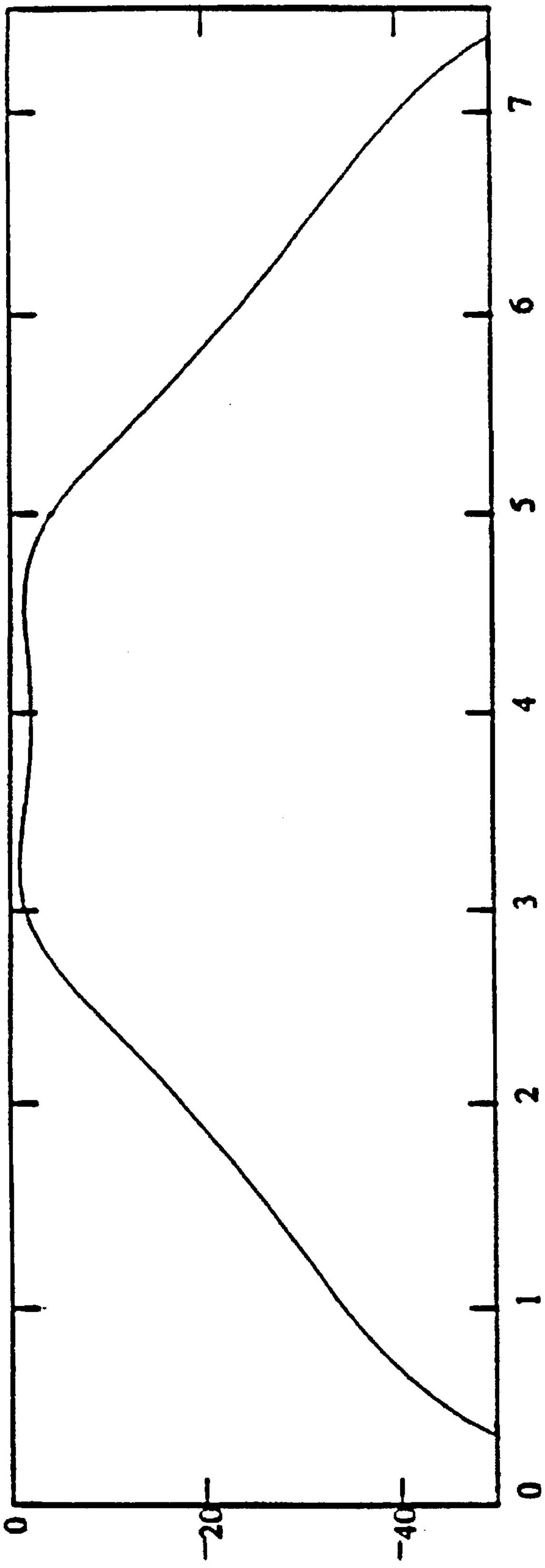
FIG. 21 is a graphical representation of the frequency domain impulse response of the embodiment of the conventional transducer of FIG. 15 with the amplitude shown in dB.

FIGS. 16 and 17 are graphs showing the rectified two-way time domain impulse response of a transducer made with the hybrid design and the conventional design respectively. The horizontal scale is in microseconds and the vertical scale is the amplitude of vibration in dB. FIGS. 18 and 19 are graphs showing the two-way time domain impulse response of the conventional transducer used to produce the graphs of FIGS. 16 and 17 respectively. The horizontal scale is in microseconds and the vertical scale is the amplitude of the received signal under two-way impulse response with units of Volts. FIGS. 20 and 21 are graphs showing the two-way frequency domain impulse response of the hybrid transducer and the conventional transducer used in obtaining the graphs of FIGS. 16–19 respectively. The horizontal scales are frequency in MHZ and the vertical scales are amplitude in dB.

The result shows that the transducer with the hybrid design structure exhibits wider bandwidth. The parameters corresponding to the performance characteristics of these two transducers are shown in Table 2.

TABLE 2

Frequency domain impulse response comparisons

| | Conventional transducer | Hybrid transducer |
|---|---|---|
| Bandwidth @−6 dB below the spectrum peak as a % of centre frequency | 69 | 97 |
| Bandwidth @−20 dB below the spectrum peak as a % of centre frequency | 108 | 142 |
| Centre frequency @−6 dB below the frequency spectrum peak | 3.76 | 3.54 |
| Centre frequency @−20 dB below the frequency spectrum peak | 3.76 | 3.7 |

The transducer with the wider bandwidth would receive and transmit ultrasonic signals more efficiently over a wider range of frequencies. For example, one advantage of a transducer with wide band frequency response is the transducer's ability to operate at two distinct resonance frequencies determined by the excitation electrical signal. The higher frequency excitation signal can be used for high resolution imaging with a shallow penetration depth due to the high attenuation. Alternatively, the operating frequency can be reduced for improved penetration but at the expense of lower resolution. The operating resonance frequency of a wide band transducer can be easily controlled by the electrical excitation signal with high efficiency.

The hybrid transducer structure also has an impulse response with a shorter ringdown time as shown in FIGS. 18–19. The shorter ringdown time would result in an improved range resolution. This improved ringdown time is better illustrated in the rectified waveform of FIGS. 16–17. Here on a logarithmic scale, the reduced ringdown time of the transducer with the hybrid ceramic structure is clearly exhibited. The sensitivity of the two transducers are also compared to one another. The peak-to-peak sensitivity of the hybrid transducer is 0.6 dB higher than that of the corresponding conventional transducer.

Although an embodiment with two piezoelectric layers is shown in the example above, it is to be understood that ultrasonic transducers having more piezoelectric layers can be constructed, applied, and analyzed by simulation in a similar manner. For example, the modes of operation of the embodiments are not exhaustive, other permutation and combination of poling vectors may be achieved. Also, each or some of the piezoelectric layers of the piezoelectric element in an embodiment of the present invention can have a thickness that is different from, or similar to one or more of the other layers. By selecting the combination of thicknesses of the piezoelectric layers in the piezoelectric element, an ultrasonic probe can be made to respond favorably to a variety of oscillation resonance frequencies. Ultrasonic probes in which the piezoelectric element has 3, 4, 5, or more piezoelectric layers can also be made based on the teaching of the present invention.

What is claimed is:

1. An ultrasonic probe for coupling acoustic signals between the probe and a medium, comprising:

(A) a piezoelectric element having a plurality of piezoelectric layers each having a different acoustic impedance, said layers being stacked in progressive order of acoustic impedance such that the layer with the acoustic impedance nearest to that of the medium is proximate the medium, wherein at least one of said layers is made of piezoelectric composite material;

(B) an electrode means for electrically coupling said piezoelectric layers to a voltage source for applying or receiving oscillation voltage potential at the piezoelectric layers, such that at least one of said layers made of piezoelectric composite material is capable of being piezoelectrically active; and (C) a control means for controlling the polarization of at least one of the piezoelectric layers.

2. The ultrasonic probe according to claim 1 further comprising an oscillation voltage means coupled to the electrode means for generating the acoustic signals.

3. The ultrasonic probe according to claim 1 wherein the ultrasonic element includes at least two layers of piezoelectric composite material each having relaxor ferroelectric ceramic.

4. The ultrasonic probe according to claim 1 wherein the ratio of the acoustic impedances between each two adjacent piezoelectric layers in the piezoelectric element is from 1:1 to 1:6.

5. The ultrasonic probe according to claim 4 wherein the ratio of the acoustic impedances between each two adjacent piezoelectric layers in the piezoelectric element is from 1:2 to 1:4.

6. The ultrasonic probe according to claim 1 wherein the piezoelectric layers in the stack are connected electrically in parallel to the oscillation voltage.

7. The ultrasonic probe according to claim 1 wherein each two adjacent piezoelectric layers of the piezoelectric element result in less than 50% difference in stress vector when under the same oscillation voltage.

8. The ultrasonic probe according to claim 7 wherein each two adjacent piezoelectric layers of the piezoelectric element result in less than 20% difference in stress vector when under the same oscillation voltage.

9. The ultrasonic probe according to claim 8 wherein each two adjacent piezoelectric layers in the piezoelectric layers result in substantially the same stress vector under the same oscillation voltage.

10. The ultrasonic probe according to claim 1 wherein the piezoelectric element has at least three piezoelectric layers, the layer with the highest acoustic impedance having higher than 30 MRayl and the layer with the lowest acoustic impedance having less than 3 MRayl.

11. The ultrasonic probe according to claim 1 wherein the piezoelectric element has at least three piezoelectric layers, at least two of the piezoelectric layers having controllable polarity and having a Curie temperature near room temperature.

12. The ultrasonic probe according to claim 11 wherein each of the piezoelectric layers in the piezoelectric element results in substantially the same stress vector under the same oscillation voltage.

13. The ultrasonic probe according to claim 1 wherein said control means includes a DC power supply for applying a DC voltage to the at least one piezoelectric layer to control the polarization thereof.

14. The ultrasonic probe according to claim 1 wherein the control means selectively applies oscillation voltage potential to excite one or more of the plurality of piezoelectric layers, at least one of said layers is made of the piezoelectric composite material.

15. An ultrasonic probe for coupling acoustic signals between the probe and a medium, comprising:

(A) a piezoelectric element having a plurality of piezoelectric layers each having different acoustic impedance, said layers being stacked in progressive order of acoustic impedance such that the layer with the acoustic impedance nearest to that of the medium is proximate the medium, wherein at least one of said layers is made of piezoelectric composite material; and (B) an electrode means for electrically coupling said piezoelectric layers to a voltage source for applying or receiving an oscillation voltage potential at the piezoelectric layers, such that at least one of said layers made of piezoelectric composite material is capable of being piezoelectrically active;

wherein each of the piezoelectric layers in the piezoelectric element results in substantially the same stress vector under the same oscillation voltage.

16. An ultrasonic probe for coupling acoustic signals between the probe and a medium, comprising:

(A) a piezoelectric element having at least three piezoelectric layers each having different acoustic impedance, at least two of said layers being adjacent to each other and made of a piezoelectric composite material including relaxor ferroelectric ceramics, said at least three layers being stacked in progressive order of acoustic impedance such that the layer with the acoustic impedance nearest to that of the medium is proximate the medium, the layer with the highest acoustic impedance having higher than 30 MRayl and the layer with the lowest acoustic impedance having less than 3 MRayl, the ratio of the acoustic impedances between each two adjacent piezoelectric layers in the piezoelectric element beings from 1:2 to 1:3, each two adjacent piezoelectric layers of the piezoelectric element result in less than 40% different in stress under the same oscillation voltage;

(B) an electrode means for electrically coupling said piezoelectric layers for applying a voltage potential thereto;

(C) a control means for controlling the polarization of at least two of the piezoelectric layers in the piezoelectric element;

(D) an oscillation voltage means coupled to the electrode means for exciting the acoustic signals, wherein the piezoelectric layers in the piezoelectric element are connected electrically in parallel to said oscillation voltage means; and (E) an ultrasonic focusing means.

17. A method of transmitting ultrasound to a target in a medium, comprising:

(A) impedance-matching with the medium by providing a probe including a piezoelectric element having at least three piezoelectric layers stacked in progressive order of acoustic impedance such that the layer with the acoustic impedance nearest to that of the medium is proximate the medium, one of said layers is made of piezoelectric composite material, said probe being capable of emitting at least three different oscillation resonance frequencies;

(B) selecting one of the at least three oscillation resonance frequencies that provides the desired results in transmitting ultrasound to the target;

(C) exciting the piezoelectric element to selectively emit the selected oscillation resonance frequency, the oscillation resonance frequency being controlled by at least one of controlling the polarization of at least one of said piezoelectric layers in said piezoelectric element and selectively applying an oscillation voltage to one or more of the piezoelectric layers to alter the oscillation resonance frequency of said piezoelectric element, such that at least one of said layers made of piezoelectric composite material is piezoelectrically active.

18. The method of transmitting ultrasound according to claim 17 wherein at least one of said piezoelectric layers includes relaxor ferroelectric ceramic.

19. The method of transmitting ultrasound according to claim 17 herein the polarization of at least one of said piezoelectric layers is controlled by applying a DC voltage thereto at ambient temperature.

20. The method of transmitting ultrasound according to claim 17 wherein the ratio of the acoustic impedances between each two adjacent piezoelectric layers in the piezoelectric element is from 1:1 to 1:6.

21. The method of transmitting ultrasound according to claim 17 wherein each two adjacent piezoelectric layers of the piezoelectric element result in less than 40% difference in stress vector under the same oscillating voltage.

22. A method of making an ultrasonic transducer, comprising:

(A) layering a plurality of piezoelectric layers and a plurality of electrodes together by interposing the piezoelectric layers between the electrodes to form a stack of piezoelectric element, each of the piezoelectric layers having a different acoustic impedance, the piezoelectric layers being layered in progressive order of acoustic impedance such that the layer with the acoustic impedance nearest to that of a medium is proximate the medium, wherein at least one of said layers is made of piezoelectric composite material;

(B) connecting the electrodes to controlling means for controlling the polarization of at least one of the piezoelectric layers; and (C) providing electrical connectors on the electrodes for connecting to an oscillation voltage for selectively activating one or more of the piezoelectric layers such that at least one of said layers made of piezoelectric composite material is capable of being piezoelectrically active.

23. An ultrasonic probe for coupling acoustic signals between the probe and a medium, comprising:

(A) a piezoelectric element having a plurality of piezoelectric layers each having a different acoustic impedance, said layers being stacked in progressive order of acoustic impedance such that the layer with the acoustic impedance nearest to that of the medium is proximate the medium, wherein at least one of said layers is made of piezoelectric composite material, at least one of which includes relaxor ferroelectric ceramic;

(B) an electrode means for electrically coupling said piezoelectric layers to a voltage source for applying or receiving an oscillation voltage potential at the piezoelectric layers; and (C) a control means for controlling the polarization of at least one of the piezoelectric layers.

24. An ultrasonic probe for coupling acoustic signals between the probe and a medium, comprising:

(A) a piezoelectric element having a plurality of piezoelectric layers each having a different acoustic impedance, said layers being stacked in progressive order of acoustic impedance such that the layer with the acoustic impedance nearest to that of the medium is proximate the medium, wherein at least one of said layers is made of piezoelectric composite material;

(B) an electrode means for electrically coupling said piezoelectric layers to a voltage source for applying or receiving an oscillation voltage potential at the piezoelectric layers; and (C) a control means for controlling the polarization of at least one of the piezoelectric layers;

wherein the ratio of the acoustic impedances between each two adjacent piezoelectric layers in the piezoelectric element is from 1:2 to 1:4.

* * * * *